US012252675B2

(12) United States Patent
Rogers et al.

(10) Patent No.: US 12,252,675 B2
(45) Date of Patent: Mar. 18, 2025

(54) TISSUE CULTURE PLATFORM HAVING MULTIPLE WELL CHAMBERS FLUIDICALLY COUPLED VIA MICROFLUIDIC CHANNELS AND SELECTOR VALVES

(71) Applicant: Northwestern University, Evanston, IL (US)

(72) Inventors: Hunter B. Rogers, Chicago, IL (US); Teresa K. Woodruff, Chicago, IL (US); Ji-Yong Julie Kim, Evanston, IL (US); Hannes Marcus Campo, Evanston, IL (US)

(73) Assignee: Northwestern University, Evanston, IL (US)

( * ) Notice: Subject to any disclaimer, the term of this patent is extended or adjusted under 35 U.S.C. 154(b) by 948 days.

(21) Appl. No.: 17/309,061

(22) PCT Filed: Oct. 16, 2019

(86) PCT No.: PCT/US2019/056615
§ 371 (c)(1),
(2) Date: Apr. 19, 2021

(87) PCT Pub. No.: WO2020/081740
PCT Pub. Date: Apr. 23, 2020

(65) Prior Publication Data
US 2022/0025308 A1 Jan. 27, 2022

Related U.S. Application Data

(60) Provisional application No. 62/746,967, filed on Oct. 17, 2018.

(51) Int. Cl.
*C12M 1/00* (2006.01)
*C12M 1/02* (2006.01)
(Continued)

(52) U.S. Cl.
CPC ............ *C12M 21/08* (2013.01); *C12M 23/12* (2013.01); *C12M 23/16* (2013.01); *C12M 23/26* (2013.01);
(Continued)

(58) Field of Classification Search
CPC ...... C12M 21/08; C12M 23/12; C12M 23/16; C12M 23/26; C12M 23/34; C12M 23/48;
(Continued)

(56) References Cited

U.S. PATENT DOCUMENTS 8,906,685 B2 12/2014 Takayama
9,222,932 B2 12/2015 Shepherd
(Continued)

FOREIGN PATENT DOCUMENTS

WO 2000017624 A2 3/2000
WO 2010031194 A1 3/2010
(Continued)

OTHER PUBLICATIONS

International Searching Authority. International Search Report and Written Opinion for application PCT/US2019/056615. Mailed on Jan. 9, 2020. 11 pages.
(Continued)

*Primary Examiner* — Liban M Hassan
(74) *Attorney, Agent, or Firm* — Quarles & Brady LLP

(57) ABSTRACT

Tissue culture platforms that may be configured for tissue culture or biological cell culture, and methods for use thereof, are described. In general, the tissue culture platforms include multiple well chambers that are fluidically coupled by one or more channels Flow between the different well chambers is controlled via one or more selector valves, enabling a single tissue culture platform that can provide multiple integrated culture subsystems, multiple non-interacting culture subsystems, or combinations thereof.

32 Claims, 11 Drawing Sheets

(51) Int. Cl.
*C12M 1/32* (2006.01)
*C12M 1/34* (2006.01)
*C12M 3/00* (2006.01)
*C12M 3/06* (2006.01)

(52) U.S. Cl.
CPC ............ *C12M 23/34* (2013.01); *C12M 23/48* (2013.01); *C12M 23/58* (2013.01); *C12M 27/00* (2013.01); *C12M 29/00* (2013.01); *C12M 41/40* (2013.01)

(58) Field of Classification Search
CPC ...... C12M 23/58; C12M 27/00; C12M 29/00; C12M 41/40; C12M 23/40; C12M 25/02
See application file for complete search history.

(56) References Cited

U.S. PATENT DOCUMENTS

| | | | |
|---|---|---|---|
| 9,243,221 | B2 | 1/2016 | Yarmush |
| 9,273,276 | B2 | 3/2016 | Shuler |
| 9,512,393 | B2 | 12/2016 | Kasuto |
| 9,575,055 | B2 | 2/2017 | Gevaert |
| 9,695,399 | B2 | 7/2017 | Woodruff |
| 9,777,252 | B2 | 10/2017 | Cuiffi |
| 9,791,433 | B2 | 10/2017 | Marx |
| 10,023,832 | B2 | 7/2018 | Wikswo |
| 2002/0133072 | A1 | 9/2002 | Wang |
| 2005/0266582 | A1 | 12/2005 | Modlin |
| 2008/0145924 | A1 | 6/2008 | Kobayashi |
| 2011/0207209 | A1* | 8/2011 | Hammons ............... C12M 23/42 435/303.1 |
| 2013/0108801 | A1 | 5/2013 | Naessens |
| 2014/0030752 | A1 | 1/2014 | Cuiffi |
| 2014/0302549 | A1 | 10/2014 | Marx |
| 2015/0298123 | A1 | 10/2015 | Block |
| 2016/0145554 | A1 | 5/2016 | Ingber |
| 2016/0145555 | A1 | 5/2016 | Ingber |
| 2016/0264918 | A1* | 9/2016 | Shimase ................ C12M 29/00 |
| 2016/0274085 | A1 | 9/2016 | Nair |
| 2017/0081625 | A1 | 3/2017 | Wikswo |
| 2017/0227525 | A1* | 8/2017 | Griffith ................... F04B 43/12 |
| 2017/0252701 | A1 | 9/2017 | Nosrati |
| 2018/0057796 | A1 | 3/2018 | Woodruff |
| 2020/0190479 | A1 | 6/2020 | Woodruff |
| 2020/0224147 | A1 | 7/2020 | Rogers |

FOREIGN PATENT DOCUMENTS

| | | |
|---|---|---|
| WO | 2014081840 A1 | 5/2014 |
| WO | 2017059436 A1 | 4/2017 |
| WO | 2017096282 A1 | 6/2017 |

OTHER PUBLICATIONS

Lee, P. J., et al. "Microfluidic system for automated cell-based assays." JALA: Journal of the Association for Laboratory Automation 12.6 (2007): 363-367.

Maschmeyer, I., et al. "A four-organ-chip for interconnected long-term co-culture of human intestine, liver, skin and kidney equivalents." Lab on a Chip 15.12 (2015): 2688-2699.

Puccinelli, J. P., et al. "Automated high-throughput microchannel assays for cell biology: Operational optimization and characterization." JALA: Journal of the Association for Laboratory Automation 15.1 (2010): 25-32.

Renggli. 2017. Microfluidic Multi-Tissue Platform for Use with Spherical Microtissues. Analytical Science Magazine. Available online at https://analyticalscience.wiley.com/do/10.1002/gitlab.15455/full/.

Tsuda, S., et al. "Customizable 3D printed 'plug and play' millifluidic devices for programmable fluidics." PLoS One 10.11 (2015): e0141640.

Vereshchagina, E., et al. "Plate reader compatible membrane-integrated microfluidic platform for high-throughput cellular assays." 2013 Transducers & Eurosensors XXVII: The 17th International Conference on Solid-State Sensors, Actuators and Microsystems (Transducers & Eurosensors XXVII). IEEE, 2013.

Virumbrales-Munoz, M., et al. "Multiwell capillarity-based microfluidic device for the study of 3D tumour tissue-2D endothelium interactions and drug screening in co-culture models." Scientific reports 7.1 (2017): 1-15.

Wagner, I., et al. "A dynamic multi-organ-chip for long-term cultivation and substance testing proven by 3D human liver and skin tissue co-culture." Lab on a Chip 13.18 (2013): 3538-3547.

Xiao, S., et al. "A Microfluidic Culture Model of the Human Reproductive Tract and 28-Day Menstrual Cycle." Nature Communications, vol. 8, 2017, p. 14584.

* cited by examiner

TISSUE CULTURE PLATFORM HAVING MULTIPLE WELL CHAMBERS FLUIDICALLY COUPLED VIA MICROFLUIDIC CHANNELS AND SELECTOR VALVES

CROSS-REFERENCE TO RELATED APPLICATIONS

This application is a national stage application of International Patent Application PCT/US2019/056615, filed Oct. 16, 2019 and claims the benefit of U.S. Provisional Patent Application Ser. No. 62/746,967, filed on Oct. 17, 2018, and entitled "TISSUE CULTURE PLATFORM HAVING MULTIPLE WELL CHAMBERS FLUIDICALLY COUPLED VIA MICROFLUIDIC CHANNELS AND SELECTOR VALVES," the contents of each of which are herein incorporated by reference in their entirety for all purposes.

STATEMENT REGARDING FEDERALLY SPONSORED RESEARCH

This invention was made with government support under ES029073 awarded by the National Institutes of Health. The government has certain rights in the invention.

BACKGROUND

Presently, a majority of cell culture and tissue culture is performed in environments that do not accurately recreate cellular environments due to a lack of 3-dimensional structure, dynamic flow, and tissue-tissue interactions. Although there have been recent technologies that have attempted to address these issues, one of the main shortcomings is the lack of compatibility of these new technologies with current laboratory hardware (e.g., microscopes), especially in terms of automated equipment often present in industrial research labs.

SUMMARY OF THE DISCLOSURE

The present disclosure addresses the aforementioned drawbacks by providing a tissue culture assembly that includes a base plate and a plurality of culture subsystems coupled to the base plate. Each culture subsystem includes a plurality of well chambers (e.g., one or more culture wells, one or more donor wells, one or more acceptor wells), a plurality of channels, and a selector valve fluidically coupling the plurality of well chambers via the plurality of channels. The selector valve is operable to modify a fluid path to facilitate exchange of media within a given culture subsystem or between culture subsystems. The tissue culture assembly can, therefore, be configured to provide a plurality of integrated culture subsystems, a plurality of non-interacting culture subsystems, or combinations thereof.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are tissue culture platforms, which may be configured for tissue culture or biological cell culture, and methods for use thereof. In general, the tissue culture platforms described in the present disclosure include multiple culture wells, donor wells, and acceptor wells that are fluidically coupled by one or more channels. Flow between the different wells is controlled via selector valves. Combinations of culture wells, donor wells, and acceptor wells can be fluidically coupled into culture subsystems, and a plurality of such culture subsystems can be fluidically coupled to enable customizable setup of multiple interconnected systems (e.g., organ systems, organoids, and so on), multiple independent culture experiments, and so on.

The tissue culture platforms described in the present disclosure address the deficiencies of both traditional and recent biological technologies by enabling three-dimensional culture of multiple interconnected cell/tissue types under dynamic flow conditions. Advantageously, the tissue culture platforms described in the present disclosure can be provided with a form factor that is similar to standard microplates, making the system compatible with current laboratory hardware.

This design and modularity of the tissue culture platforms described in the present disclosure allows for in vitro tissue models to be co-cultured in a way that is more capable of replicating in vivo interactions between different tissues, organs, or both. By linking tissue models together via fluidic channels, the tissue culture platforms described in the present disclosure better replicate the complex tissue-tissue interactions seen in vivo (e.g., by mimicking how in vivo tissues are linked via the circulatory system) that are important to physiology. The introduction of fluid flow also exposes tissues and cells to important biological and physical phenomena (e.g., fluidic shear stress, chemical gradients) and improves waste elimination, which creates healthier in vitro cultures that can be sustained for longer periods of time compared to traditional culture methods.

The tissue culture platforms described in the present disclosure can be generalized for use with any number of different formats. For instance, they can be used with cell monolayers, explants, spheroids, 3D-printed scaffolds, other cell or tissue formats, and combinations thereof. The tissue culture platforms can be used for single tissue experiments, or can also enable multi-tissue capacity, such that organ systems and interactions between organ systems can be modeled.

Figure 1:
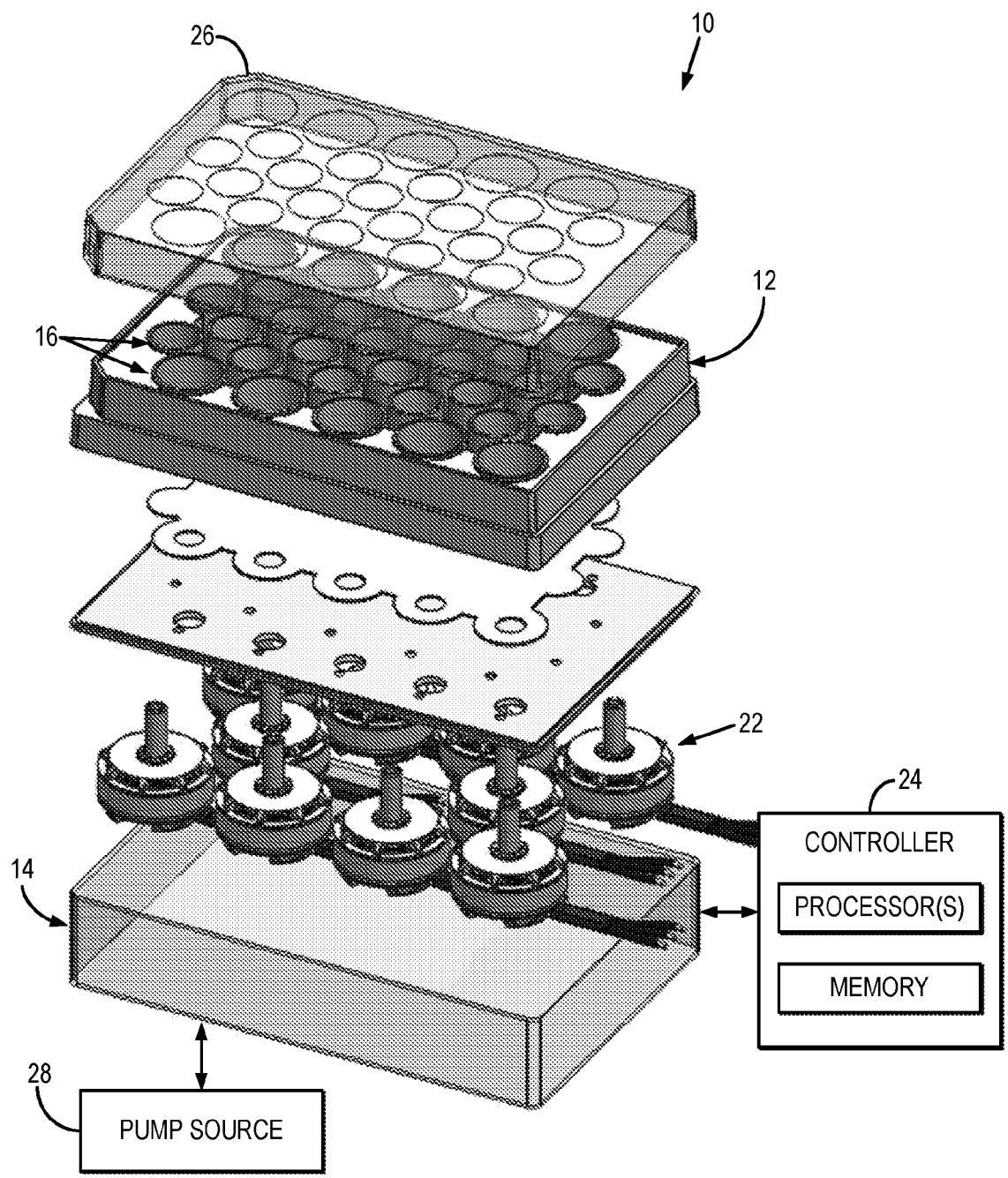
FIG. 1 shows an example of a tissue culture assembly in accordance with some embodiments described in the present disclosure.
Figure 2:
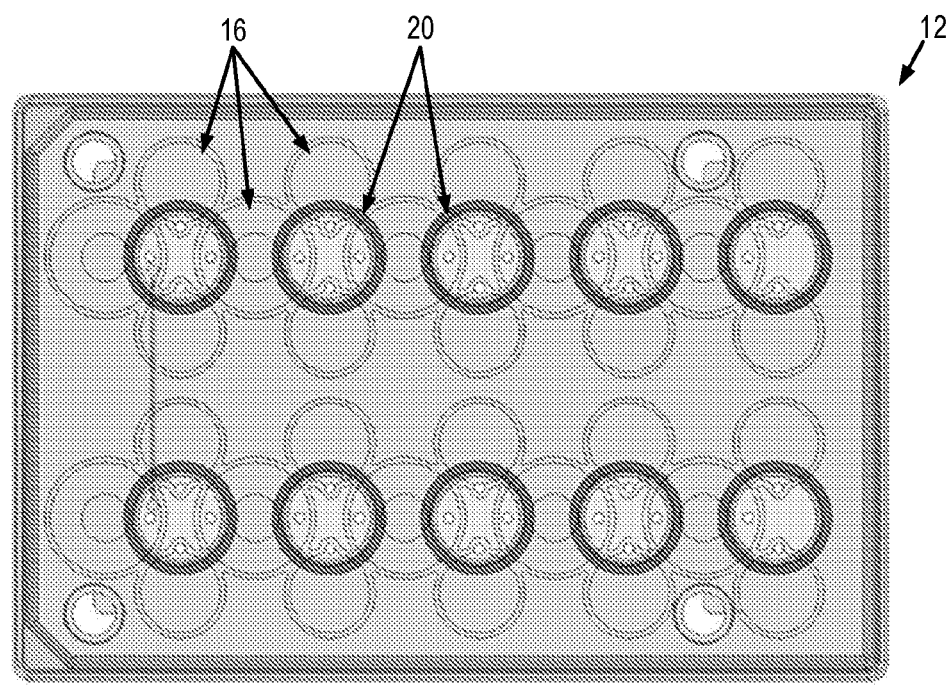
FIG. 2 shows an example of a disposable base plate that forms a part of a tissue culture assembly in accordance with some embodiments described in the present disclosure.
Figure 3:
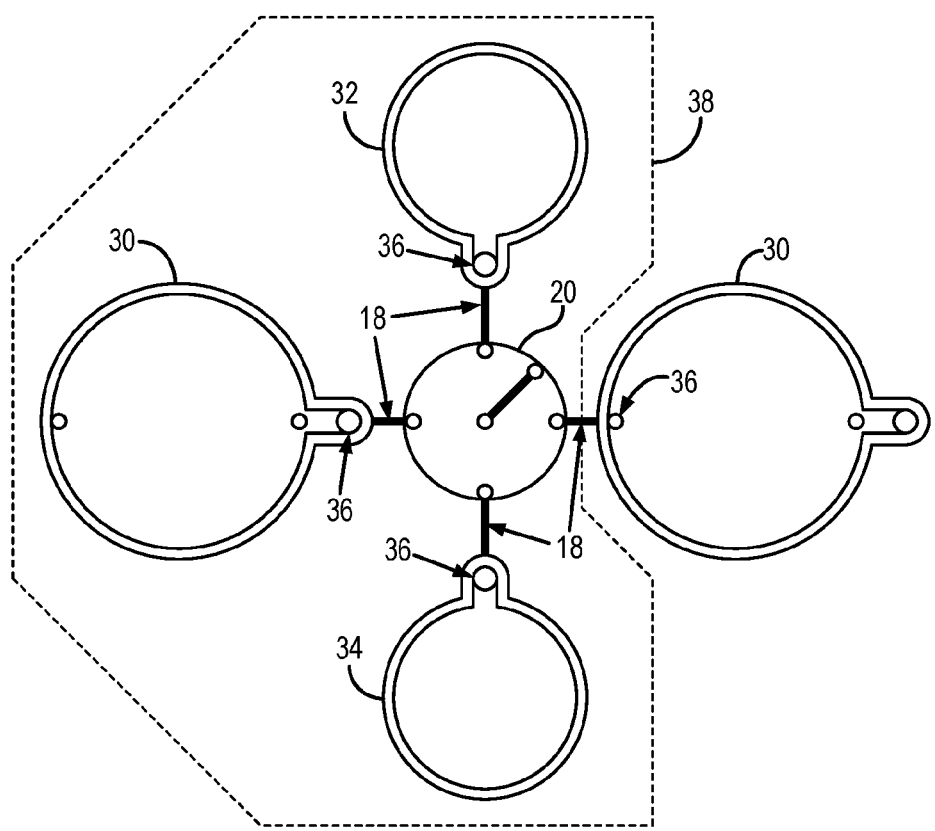
FIG. 3 shows an example of multiple well chambers that are fluidically coupled via channels that define different fluid paths between the well chambers, which are selected using a common selector valve.

As shown in FIGS. 1-3, a tissue culture platform 10 can include a base plate 12, which may be a disposable base plate, and a base station 14, which may be a reusable base station. For instance, the base station 14 can be installed semi-permanently within an incubator (e.g., a cell culture incubator), and the base plate 12 can be a disposable base plate that is designed for single experiments. In other implementations, the base station 14 is not installed within an incubator, but is a free standing device that can be loaded and unloaded from an incubator as needed or otherwise desired.

The base plate 12 can include a plurality of well chambers 16 that are fluidically coupled by channels 18, which may be microfluidic channels, for cell/tissue culture. Flow of media between the well chambers 16 is modified or otherwise controlled using selector valves 20 that change or otherwise modify the fluid path between the well chambers 16. In some embodiments, the base plate 12 can be a plate of a suitable material that is sized and shaped for the desired application. Non-limiting examples of such materials, sizes, and shapes are described below in more detail. As also described below, in some instances well chambers 16 can be formed in the base plate 12, while in some other instances the well chambers 16 can be removably coupled to the base plate 12.

The base station 14 may include an enclosure housing one or more motors 22 for adjusting the selector valves 20 and electronics, such as a controller 24. The controller 24 can be configured to control operation of the selector valves 20 and motors 22 to facilitate fluid flow between the well chambers 16, as well as plate attachment/detachment. The controller 24 may include, for example, one or more processors and a memory having instructions stored thereon that, when executed by the one or more processors, provide for flow control in the tissue culture platform 10 through selective operation of the selector valves 20.

In some embodiments, a removable lid 26 is provided and can be used to cover or otherwise enclose the base plate 12. The removable lid 26 can be a disposable lid, and can be removed manually or by automated robotic handling. In some instances, the lid 26 can be made from a transparent material to facilitate imaging of the well chambers 16.

As will be described below in more detail, the selector valves 20 may in some instances be pneumatically actuated selector valves. In such instances, a pump source 28 can be arranged in the base station 14. The pump source 28 is operable to pump fluid (e.g., air) to the selector valves 20 in order to actuate the selector valves 20 to modify the flow therethrough. As one example, the pump source 28 can be a syringe pump that pumps air, or another suitable fluid, to the selector valves 20 in order to actuate the valves. In these instances, the pump source 28 is operable to provide negative and positive pressure to a reservoir in the selector valve 20, which results in deflection of a flexible membrane and subsequent fluid flow through the selector valve 20.

A selector valve 20 is generally operable to define an open state and a closed state. In the open state, the selector valve 20 modifies the fluid path to fluidically couple a first well chamber to a second well chamber via the channels 18 that are in fluid communication with the selector valve 20 and the first and second well chambers. As noted, the first well chamber and the second well chamber may be in the same culture subsystem or in different culture subsystems. In the open state, the selector valve 20 may also modify the fluid path to provide recirculation in a selected well chamber. The selector valve 20 may also be operable to modify a flow rate or flow volume when in the open state. For instance, the selector valve 20 may enable modifying the flow rate through the selector valve 20 over a continuous range of flow rates, or may have discrete increments of different selectable flow rates. Likewise, the selector valve 20 may enable modifying the flow volume when in the open state. As another example, the selector valve 20 can be operable to enable a particular volume to be achieved in the well chamber 16.

As noted, the tissue culture platforms 10 described in the present disclosure generally include a plurality of well chambers 16, which may include a number of culture wells 30, a number of donor wells 32, and a number of acceptor wells 34. For instance, the tissue culture platform 10 can be configured to have the same number of culture wells 30, donor wells 32, and acceptor wells 34 such that each culture well 30 is fluidically coupled to one donor well 32 and one acceptor well 34. In other configurations a given culture well 30 may be fluidically coupled to more than one donor well 32, more than one acceptor well 34, or to other suitable well chambers 16. For instance, each culture well 30 can be fluidically coupled to one or more donor wells 32, one or more acceptor wells 34, an upstream culture well 30, and a downstream culture well 30 via channels 18 and a selector valve 20. Alternatively, different combinations of culture wells 30, donor wells 32, acceptor wells 34, or other well chambers 16 can be fluidically coupled via channels 18 and one or more selector valves 20.

The selector valve 20 allows the fluid path to be independently modified from each culture well 30, such that the flow of media between well chambers 16 in the tissue culture platform 10 can be controlled and modified as desired. For instance, a given selector valve 20 can be operable to modify the flow of media between a given culture well 30, a donor well 32, an acceptor well 34, and an upstream or downstream culture well 30.

The tissue culture platforms 10 described in the present disclosure can, in general, include a base plate 12 having coupled thereto a plurality of culture subsystems 38. A culture subsystem 38 can include, for example, a plurality of well chambers 16, a plurality of channels 18, and at least one selector valve 20 fluidically coupling the plurality of well chambers 16 via the plurality of channels 18. The plurality of well chambers 16 in a given culture subsystem 38 generally includes one or more culture wells 30, one or more donor wells 32, and one or more acceptor wells 34. Additionally or alternatively, the plurality of well chambers 16 can include one or more other wells. As one example, the plurality of well chambers 16 in a given culture subsystem 38 can include one culture well 30, one donor well 32, and one acceptor well 34. The selector valve 20 is operable to modify a fluid path to facilitate the exchange (e.g., flow) of media within a culture subsystem 38 (e.g., from a donor well 32 to a culture well 30, from a culture well 30 to an acceptor well 34, recirculation within a culture well 30), between culture subsystems 38 (e.g., from an upstream culture well 30 to a down stream culture well 30), or both.

By selectively controlling the flow of media within culture subsystems 38, between culture subsystems 38, or both, the tissue culture platform 10 can be configured to provide single tissue culture experiments, or multiple tissue co-culture experiments. In some configurations, the selector valves 20 can be operable to configure a tissue culture platform 10 to culture multiple tissues at once in an integrated fashion. In some other configurations, the selector valves 20 can be operable to configure a tissue culture platform 10 to culture tissues in a non-interacting manner. It will be appreciated that in still other configurations, a combination of both one or more integrated culture experiments and one or more non-interacting culture experiments can be provided with a single tissue culture platform 10.

As one non-limiting example, a tissue culture platform 10 can be constructed with ten culture subsystems 38, each containing one culture well 30, one donor well 32, and one acceptor well 34, as shown for instance in FIG. 2. In this example, the tissue culture platform 10 can be configured for a single 10-tissue experiment, two independent 5-tissue experiments, five independent 2-tissue experiments, ten independent 1-tissue experiments, or other such combinations of independent tissue experiments. Thus, in general, a tissue culture platform 10 having N different culture subsystems 38 can be configured for a single N-tissue experiment, N independent 1-tissue experiments, or some combination of independent and co-culture tissue experiments. The versatility and high degree of configurability of the tissue culture platforms 10 described in the present disclosure provide significant advantages and efficiency for performing various different tissue, or cell, culture experiments using a single platform.

Advantageously, the tissue culture platforms 10 described in the present disclosure can be sized and shaped to be compatible with standard laboratory automation hardware, including robotic handling, liquid handling, and imaging or other measurement systems. As one example, a tissue culture platform 10 can be sized and shaped for imaging in an incubator using traditional imaging systems, such as microscopic imaging systems. In some configurations, on-board imaging or measurement can be incorporated into the tissue culture platforms 10.

Whereas traditional macroscopic tissue and cell culture systems implement static well conditions, the tissue culture platforms 10 described in the present disclosure enable the flow of media between different well chambers 16. Particularly, intermittent (e.g., scheduled or otherwise regulated) or continuous flow through the tissue culture platform 10, or portions thereof, can be achieved. For instance, continuous perfusion of media through the tissue culture platform 10, or portions thereof, can be implemented in order to create chemical gradients across the well chambers 16. The ability of the tissue culture platform 10 to provide intermittent or continuous flow also enables recreating other biological or physiological conditions, including fluidic shear stress.

The well chambers 16 can be fabricated as part of the base plate 12. Alternatively, all or a portion of the well chambers 16 can be separate from, but coupled to, the base plate 12. As one example, the well chambers 16 can be separate from the base plate 12, but can reside within recesses formed in the upper surface of the base plate 12. For instance, the well chambers 16 can be configured to couple to insertion points formed in the upper surface of the base plate 12.

In some implementations, the well chambers 16 may include TRANSWELL® permeable supports, or other such permeable supports. In these instances, additional tubing or channels can be provided in the well chamber 16 in order to fluidically couple both the well chamber 16 and the TRANSWELL® permeable support or other permeable support to the channels 18.

Although the tissue culture platform 10 is described above as containing a base plate 12, in some configurations the tissue culture platform 10 does not include a base plate 12. As one example, the tissue culture platform 10 can include a plurality of physically separate well chambers 16 that are fluidically coupled by channels 18. In some instances, individual or multiple well chambers 16 may be coupled to a smaller base plates, such that well chambers 16 can be arranged into tiled arrays, allowing for the modular construction of complex networks of well chambers 16 and culture subsystems 38. In some other instances, individual well chambers 16 can simply be freestanding.

As another example, the tissue culture platform 10 can include a plurality of physically separate culture subsystems 38. As one example, the tissue culture platform 10 can include a plurality of physically separate culture subsystem 38 that are fluidically coupled by channels 18. In some instances, individual or multiple culture subsystems 38 may be coupled to a smaller base plates, such that culture subsystems 38 can be arranged into tiled arrays, allowing for the modular construction of complex networks of culture subsystems 38. In some other instances, individual well chambers 16 can simply be freestanding.

In those instances where the tissue culture platform 10 does not include a base plate 12 to which well chambers 16 are coupled, the channels 18 may include tubing, or other suitable fluidic connections, fluidically coupling the well chambers 16. Also, in these instances the base station 14 can be configured to interface with the well chambers 16 and channel 18 other than through a base plate 12. For instance, the selector valves 20 can be coupled to the base station 14, but still fluidically coupled to the channels 18. As another example, the selector valves 20 can be physically separate from the base station 14 while still fluidically coupled to the channels 18. For instance, the selector valves 20 could be coupled to or otherwise adjacent the well chambers 16 or culture subsystems 38. As an example, when the well chambers 16 or culture subsystems 38 are coupled to smaller base plates that can be arranged into modular, tiled arrays, the selector valves 20 can be coupled to these smaller base plates.

In still other examples, the base plate 12 can be replaced with another suitable base structure to which the well chambers 16 are coupled, or in which the well chambers 16 can be formed. For example, the base plate 12 could be replaced with a vessel, a tub, a reactor, a tube, a bubble, or other suitable structure to which one or more well chambers 16 or culture subsystems 38 are coupled, or in which one or more well chambers 16 or culture subsystems 38 are formed or arranged. In these instances, the base station 14, selector valves 20, or both, can be designed to couple to the vessel, tub, reactor, tube, bubble, or other suitable structure. Additionally or alternatively, in these instances the channels 18 can be formed in the vessel, tub, reactor, tube, bubble, or other suitable structure (e.g., the channels 18 may be microfluidic channels formed in the respective structures). As described above, the channels 18 may also be separate from the underlying structure, such as tubes fluidically coupling the well chambers 16, culture subsystems 38, or both.

As noted, the well chambers 16 generally include a plurality of culture wells 30, a plurality of donor wells 32, and a plurality of acceptor wells 34. The well chambers 16 are arranged over the surface of the base plate 12 in a manner that facilitates fluidically coupling the well chambers 16 to provide a network of integrated culture wells, non-interacting culture wells, or both.

The donor wells 32 can contain media (e.g., liquid) to be provided to one or more downstream culture wells 30. For example, the media may include growth media, factors (e.g., hormones), fluid reagents, and so on. The acceptor wells 34 can receive spent media (e.g., liquid) from one or more upstream culture wells 30. For example, the spent media may include waste media, fluid reagents, and excretions from the tissue or cell culture, such as enzymes and the like.

The well chambers 16 are fluidically coupled via a plurality of channels 18. The channels 18 may be microfluidic channels, which may be formed in the base plate 12. Alternatively or additionally, the channels 18 may include tubing. A microfluidic channel may have a channel width perpendicular to a longitudinal axis of the channel (i.e., a path along which fluid flows during ordinary operation) that is about 1 mm or smaller. In general, the channel width depends on the particular application. For example, channel widths may range, in certain non-limiting embodiments, from about 200 µm to about 1200 µm from about 300 µm to about 1100 µm, from about 400 µm to about 1000 µm, or from about 400 µm an to about 600 µm. The cross-sections of the microchannels (perpendicular to the respective longitudinal axes) may be rectangular, round, or have any other shape, and may (but need not) vary in size or shape along the longitudinal axes The channels 18 can be fluidically coupled to ports 36 in the well chambers 16. Flow of media between well chambers 16 is thereby modified or otherwise controlled by operating a selector valve 20 to open a fluid path from a first port 36 in a first well chamber 16 to a second port 36 on a second well chamber 16 via the channels 18 fluidically coupling the first port 36 to the second port 36. In some instances, flow through this opened fluid path can be modified or otherwise controlled by adjusting the amount of flow allowed through the selector valve 20. As noted above, in some implementations one or more of the well chambers 16 may include TRANSWELL® or other permeable supports. In these instances, such well chambers 16 may be fluidically coupled to the channels 18 via one or more additional tubes, channels, ports, or other suitable structures. For instance, the well chamber 16 may include an upper port and a lower port, thereby facilitating the addition and removal of media from the well chamber 16 with or without a TRANSWELL® or other permeable support present in the well chamber 16.

Figure 4A:
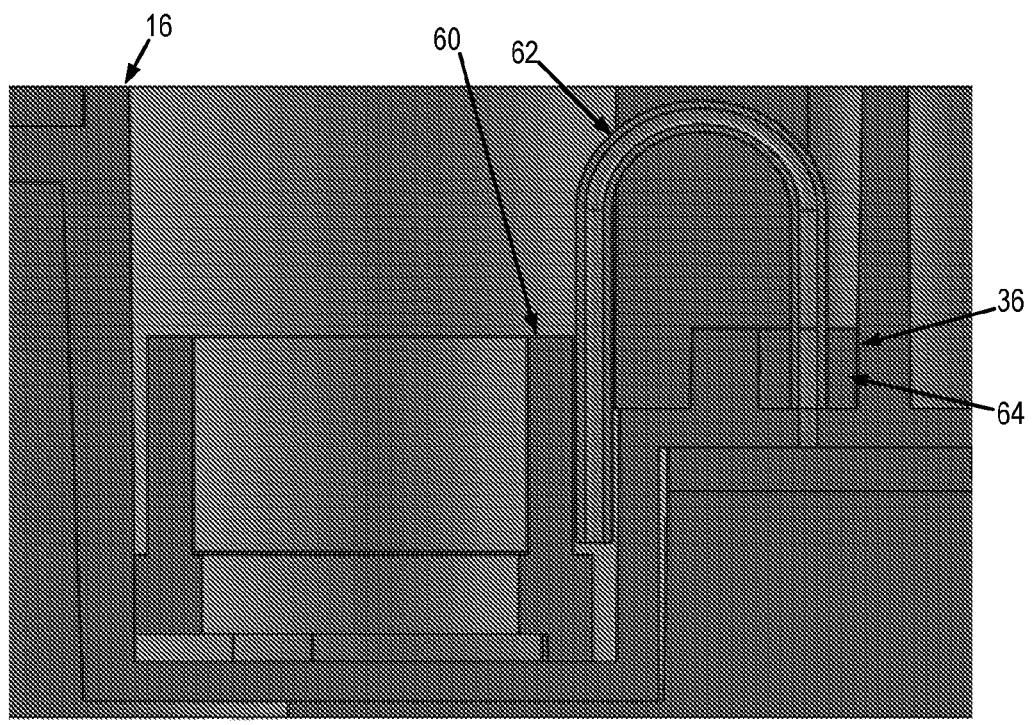
FIGS. 4A and 4B show an example of a well chamber in which a permeable support has been placed, and a corresponding tube that can be used to fluidically couple the well chamber to channels in the tissue culture platform.
Figure 4B:
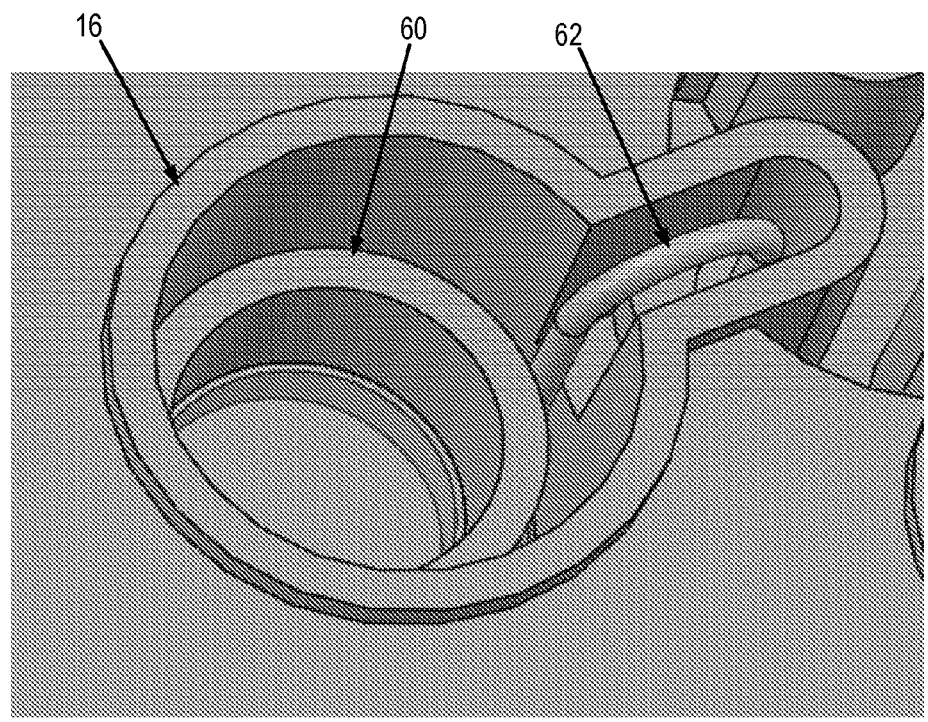

One non-limiting example of a well chamber 16 containing a permeable support 60 is shown in FIGS. 4A and 4B. In this example, a tube 62 is fluidically coupled to a port 36 at one end of the tube 62 such that the other end of the tube 62 extends into the well chamber 16. In this way, a fluid path is provided from a channel 18 to the well chamber 16 via the tube 62 and port 36. The tube 62 can be positioned adjacent an exterior surface of the permeable support 60, or can be positioned within an interior volume of the permeable support 60. For instance, the tube 62 can be a flexible tube such that its position can be adapted as needed or desired by a user. As shown in FIGS. 4A and 4B, the fluidic coupling of the tube 62 to the port 36 can include an annular stopper 64 having an outer diameter that is sized to make a seal with the inner diameter of the port 36. The tube 62 then extends through the inner aperture of the annular stopper 64. In other configurations, the outer diameter of the tube 62 can be sized and shaped to provide a seal with the inner diameter of the port 36, such that an additional stopper is not needed.

In general, the well chambers 16 may be coupled to an upper surface of the base plate 12 and the selector valves 20 may be coupled to a lower surface of the base plate 12 that is opposite the upper surface. The connection between the selector valves 20 and the base station 14 can be designed so that the base plate 12 can easily be removed manually or using automated robotic handling.

In some configurations, the dimensions and geometry of the base plate 12 can be made similar to that of standard microplates currently used in combination with laboratory automation equipment. Advantageously, this design enables the tissue culture platform 10 to be compatible with standard laboratory hardware systems. As one example, the base plate 12 can be constructed to have standard microplate base dimensions, which can include a width of 85.5 mm and a length of 127.8 mm. As another example, the base plate 12 can be constructed to have standard microplate dimensions, which can include a width of 85.5 mm, a length of 127.8 mm, and a height of 14.2 mm. As still another example, the base plate 12 can be constructed to have standard deep-well microplate dimensions, which can include a width of 85.5 mm, a length of 127.8 mm, and a height of 21.5 mm. It will be appreciated that the base plates 12 described in the present disclosure can also have dimensions other than those stated above while still providing the advantage of a dynamic tissue culture system.

Each of the well chambers 16 can be a fully enclosed, or partially enclosed, space or compartment that is capable of containing solid reagents, solid components, fluid reagents, fluid components, or combinations thereof. The well chambers 16 can have the same volume, or can have different volumes. For instance, a culture well 30 may have a larger volume than either or both of a donor well 32 and an acceptor well 34. A well chamber 16 may have a volume that is from about 1 µL to more than 10 mL. For example, well chamber volumes may range, in certain non-limiting embodiments, from about 1 µL to about 40 µL, from about 40 µL to about 100 µL, from about 100 µL to about 400 µL, from about 400 µL to about 1 mL, from about 1 mL to about 10 mL, or greater than 10 mL. In some examples, the well chambers can have volumes of 190 µL, 360 µL, 1.6 mL, 3.4 mL, 6.9 mL, 16.8 mL, or combinations thereof. Using the selector valves 20, the volume in each well chamber 16 and the volume transfer between well chambers 16 can be independently controlled.

As noted above, the flow or otherwise transfer of fluids into or out of a well chamber 16 can be regulated via one or more ports 36. The plurality of well chambers 16 can include a plurality of culture wells 30, a plurality of donor wells 32, and a plurality of acceptor wells 34. Each culture well 30 can be an enclosed space or compartment in which cells, tissues, or both, can be cultured. Each donor well can be an enclosed space or compartment capable of holding and dispensing fluid reagents. Each acceptor well can be an enclosed space or compartment capable of receiving and holding fluid reagents.

In some embodiments, one or more of the well chambers 16 can be divided by one or more permeable dividers (e.g., membranes). In such embodiments, cells may be contained within a permeable compartment within a well chamber 16 to constrain the cells (e.g., for aggregate or spheroid formation), to prevent outflow of cells, and so on.

As one example, one or more of the well chambers 16 can include permeable supports (e.g., TRANSWELL® or other permeable support-like chambers). In a permeable support, cells are confined to one portion of the well chamber 16, but media, nutrients, hormones, reagents, and so on, may pass beyond the permeable support into a second portion of the well chamber 16.

For example, a permeable-support chamber may include a flat-bottomed, open-topped, lower compartment with impermeable bottom and sides, and an upper compartment with a microporous membrane (or other permeable surface) that forms the bottom of the upper compartment. The permeable support chamber may have a closed top or a removable lid. In use, cells (e.g., a first type of cells) are placed on the upper surface of the microporous membrane within the upper compartment. The upper compartment is inserted into the lower compartment. Due to the permeability of the support, media, nutrients, factors, and so on, are able to traverse the membrane, but the cells cannot. In some embodiments, cells may also be placed in the lower chamber (e.g., a second type of cells). Other multi-chamber culture systems (e.g., two or more chambers) can be used. The divisions between chambers may be permeable, semipermeable with a particular molecular weight cutoff (e.g., permeable to small molecules, but not proteins), or impermeable.

As described above, the well chambers 16 can each include one or more ports 36. In some embodiments, the ports 36 are positioned on the well chambers 16 to allow the movement of media, nutrients, soluble factors, proteins, hormones, and so on, but not the cells within the well chambers 16. The ports 36 can include filters, membranes, or other selectively permeable materials to allow the transfer of media between well chambers 16, but to prevent the transfer of cells, tissues, or both, outside of the desired culture subsystem 38.

Figure 5A:
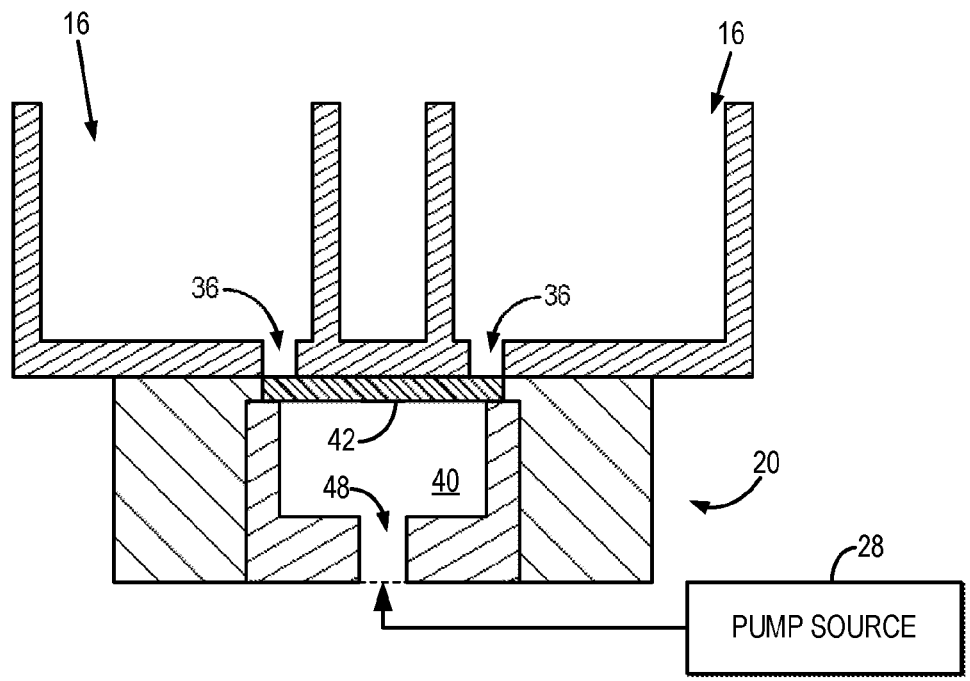
FIGS. 5A and 5B show an example operation of a pneumatically actuated selector valve to open a fluid path to fluidically couple two different well chambers.
Figure 5B:
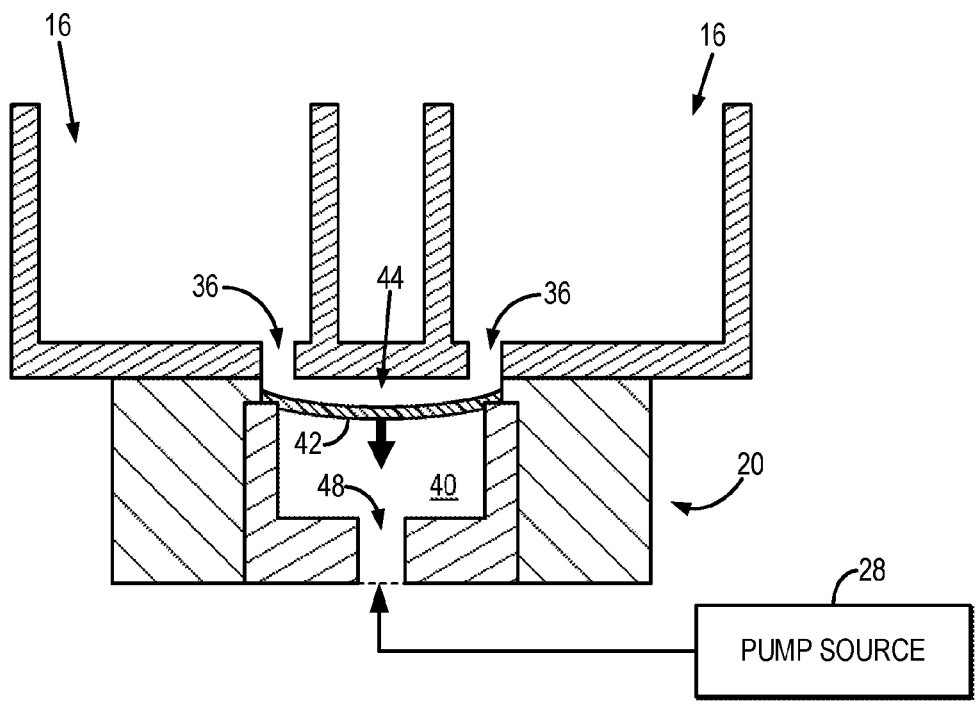

The selector valves 20 can be pneumatically actuated selector valves. In these instances, each selector valve 20 contains a small volume reservoir 40 that is used to provide fluid flow by way of a flexible membrane 42, as shown in FIGS. 5A and 5B. As one example, the reservoir 40 can have a volume between 10-200 nt. The flexible membrane 42 can be composed of an elastomer or other suitably flexible or elastic material. Negative and positive pressure is provided to the reservoir 40 by controlling air flow, or other fluid flow, into the reservoir 40 from a pump source 28. The change in pressure results in the deflection of the flexible membrane 42, which opens a fluid path 44 through the selector valve 20. For instance, deflection of the flexible membrane 42 open a fluid path 44 between a first port 36 in a first well chamber 16 and a second port 36 in a second well chamber 16. In some configurations, the fluid path 44 is additionally or alternatively defined by the channels 18 that fluidically couple the well chambers 16 with the selector valve 20.

By controlling the air flow, or other fluid flow, into the reservoir 40, the change in pressure can be controlled to modify the amount of deflection of the flexible membrane 42. As a result, the flow rate through the fluid path can be controlled. As one non-limiting example, the selector valve 20 can be operable to provide flow rates down to 25 µL per minute.

In some other implementations, the selector valves 20 may include valves that can be opened and closed using electromagnetic actuation or mechanical actuation. As one example, the selector valves 20 may be operable using a piezoelectric actuator or another suitable linear actuator.

The pump source 28 can include a piezoelectric pump, an electromagnetic actuation-based pump, a pneumatic actuation-based pump, a peristaltic pump, a centrifugal pumps, an impedance pump, and so on. In some embodiments, other techniques for facilitating flow (e.g., between well chambers 16) can be used, including gravity-driven flow, wicking, capillary action, and so on.

Figure 6:
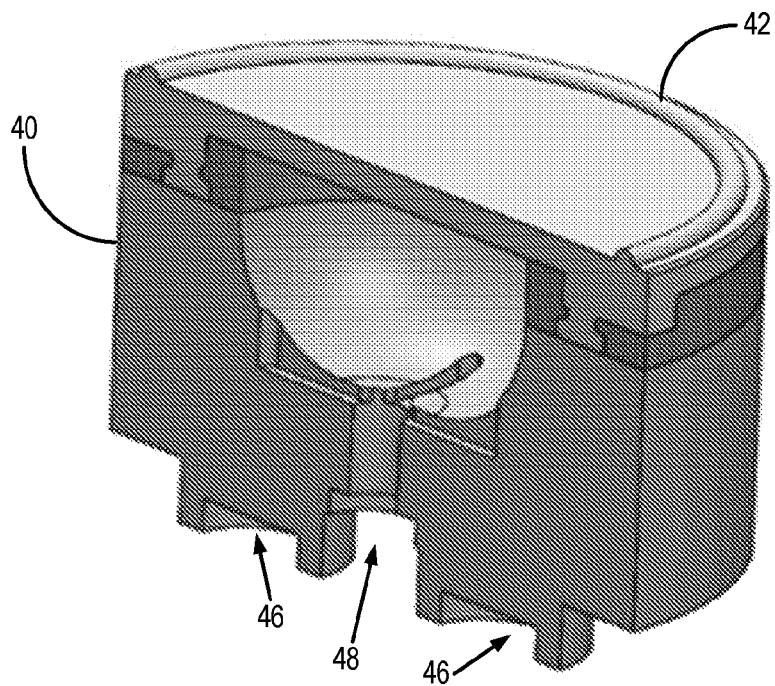
FIG. 6 shows an example of a reservoir and flexible membrane that can form a part of a selector valve.
Figure 7:
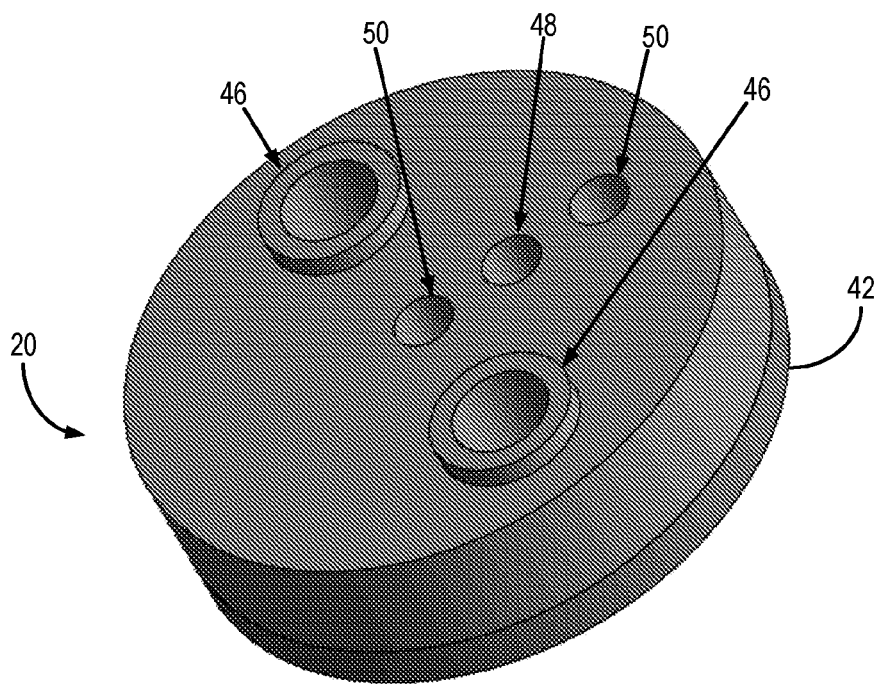
FIG. 7 shows an example of a selector valve.
Figure 8:
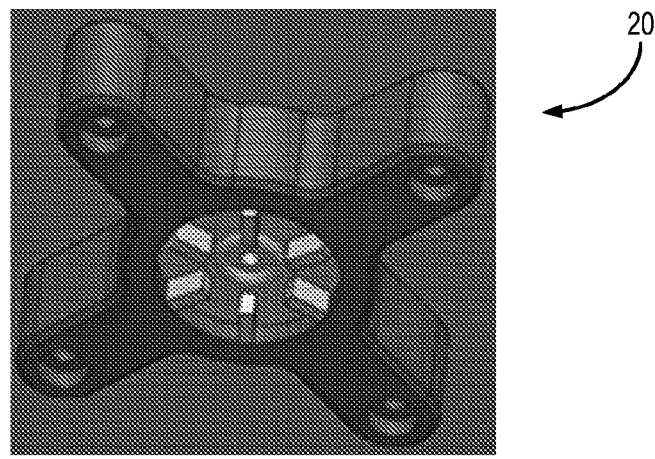
FIG. 8 shows an example of a selector valve configured as a rotary valve.

FIG. 6 shows an example of a reservoir 40 and flexible membrane 42 that may form a part of a selector valve 20. FIG. 7 shows a bottom surface of an example selector valve 20. In this configuration, the selector valve 20 includes one or more motor interfaces 46 for coupling one or more motors 22 to the selector valve 20. For example, the motor interfaces 46 may include recesses for receiving a portion of a motor 22, such that operation of the motor 22 causes the selector valve to adjust from a first position defining a first fluid path to a second position defining a second fluid path. As one example, the selector valve 20 may be a rotary valve, as shown in FIG. 8, and operation of the motor 22 can cause the rotary valve to rotate between the first position and the second position.

The selector valve 20 may also include a pump interface 48 that fluidically couples the reservoir 40 to the pump source 28. The selector valve 20 may also include one or more valve interfaces 50.

Figure 9:
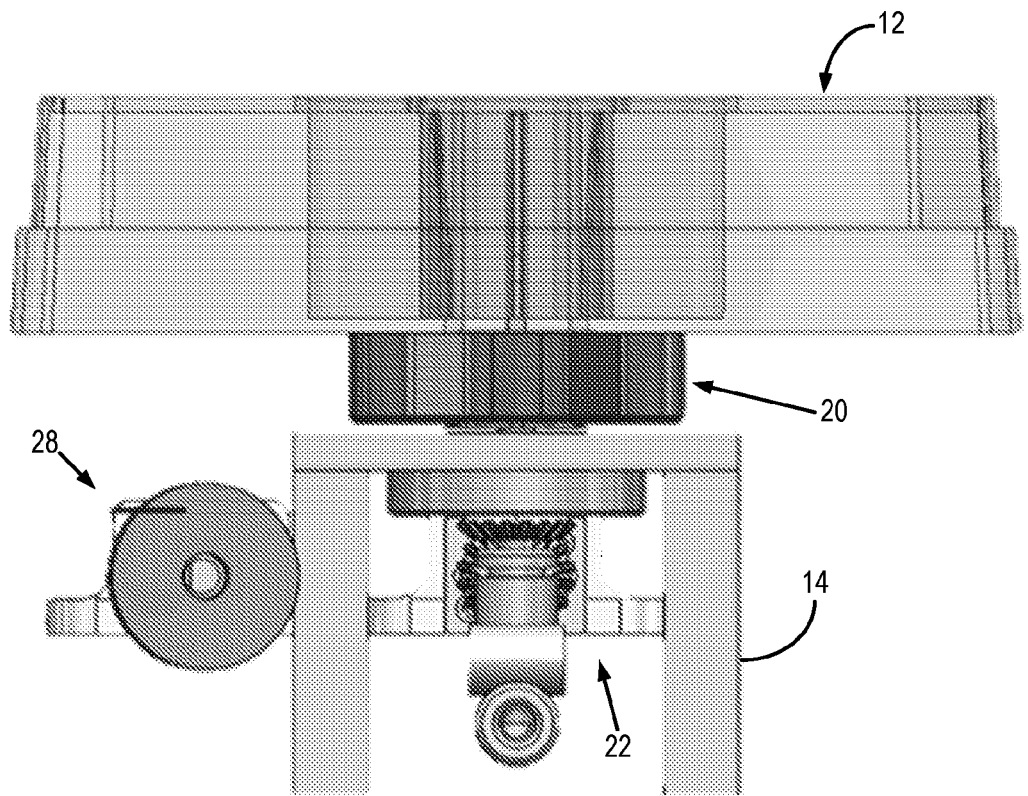
FIG. 9 shows an example of a rotary valve coupled to a disposable base plate and a reusable base station.

As shown in FIG. 9, the selector valve 20 is located on the bottom surface of the base plate 12 and connects to the base station 14, which contains one or more motors 22 for adjusting the selector valve 20 to select a desired fluid path between well chambers 16, which may include providing no fluid path between well chambers 16 or providing recirculation in a selected well chamber 16. As one example, the selector valves 20 can include rotary valves that are rotated by the one or more motors 22. In these instances, rotation of the selector valve 20 results in changing the fluid path such that different well chambers 16 are fluidically coupled by the fluid path.

Using the selector valves 20, fluid paths can be defined between well chambers 16 such that the tissue culture platform 10 defines multiple integrated culture subsystems 38, multiple non-interacting culture subsystems 38, or combinations thereof. When configured to include integrated culture subsystems 38, the tissue culture platform 10 can include well chambers 16 that are in fluid communication with each other via bidirectional, unidirectional, or continuous flow or exchange of media, with mixing or without mixing. In some embodiments, the tissue culture platform 10 is designed to provide appropriate culture conditions (e.g., media, temperature) for each culture subsystem 38.

The tissue culture platforms 10 described in the present disclosure can be configured to include multiple integrated, or otherwise interacting, culture subsystems 38. In these instances, flow or exchange between different culture subsystems 38 allows for downstream cell or tissue types to respond to factors secreted by upstream cell or tissue types in real time. Such a tissue culture platform 10 mimics the dynamic in vivo systems and communication between tissue types that are present in whole organisms.

In some embodiments, culture subsystems 38, are connected in series (e.g., one culture subsystem upstream from a second culture subsystem). In other embodiments, two or more culture subsystems 38 are connected in parallel (e.g., two or more culture subsystems downstream and upstream from the same culture subsystems). In some embodiments, two or more culture subsystems 38 are connected in semi-parallel (e.g., downstream or upstream from the same culture subsystems, but in series with one or more other culture subsystems). In general, the tissue culture platforms 10 described in the present disclosure can be configured with any suitable configuration and connectivity of culture subsystems 38 or well chambers 16 therein.

As described, the tissue culture platforms 10 described in the present disclosure can be configured for dynamic culture (e.g., continuous and/or regulated flow into and/or out of a culture well 30) to allow for the transfer of factors from one culture subsystem 38 to another, thereby enabling the transfer of factors within complex body systems. In this manner, otherwise static cultures, in which the necessary factors are added by a user or automated system, are converted into dynamic systems in which cells, tissues, or both, are able to communicate as they do in vivo, and with real-time transfer (e.g., downstream delivery) of hormones and other factors between tissues. Advantageously, the tissue culture platforms 10 can be operated for any number of suitable run times. A tissue culture platform 10 may be operated with a run time that is from about 1 second to days, weeks, months, or more. For example, run times may be on the order of a few seconds, a few minutes, a few hours, a few days, a few weeks, a few months, and so on, depending on the desired experiment.

The tissue culture platforms 10 described in the present disclosure can be configured to mimic the natural state of cells and/or the predictive value of assays performed therewith. In some embodiments, a network of channels 18 (e.g., microfluidic channels) connect segregated well chambers 16. Alternatively or additionally, the geometry and connectivity of the well chambers 16 can be designed to provide cellular interactions, liquid flow, and liquid residence parameters that correlate with those found for the corresponding cells, tissues, or organs in vivo.

The well chambers 16 can be designed or otherwise selected based on the type of cell or tissue to be cultured and based on the type of culture (e.g., cell monolayer, explant, spheroid, 3D-printed scaffold). In some embodiments, well chambers 16 can have any suitable shape (e.g., cylindrical, cubic) with one or more ports 36. The well chambers 16 can be shaped to have geometries that are optimized to facilitate a particular type of cell culture. For example, the well chambers 16 may have a flat or concave bottom. A given well chamber 16 may also include multiple different wells.

The tissue culture platforms 10 described in the present disclosure can be used for the simultaneous culture of two or more cells or tissues in separate culture wells 30 while allowing communication between the culture wells 30 via the transfer of sufficiently small or soluble agents and reagents (e.g., media, buffer, small molecules, hormones, peptides, proteins) between the well chambers 16. In some embodiments, the communication (e.g., fluid transfer) between the culture wells 30 allows for mimicry of in vivo conditions, whole organism conditions, or both.

Different cells types of a tissue, organ, body system, and so on, can be cultured in the tissue culture platforms 10 described in the present disclosure in order to replicate the in vivo conditions of the respective tissue, organ, body system, and so on. For example, multiple cell or tissue types may be cultured in a tissue culture platform 10 to replicate, for example, a reproductive system, a cardiac system, a nervous system, a circulatory system, a respiratory system, a digestive system, a urinary or excretory system, an integumentary system, a muscle system, a skeletal system, an endocrine system, an immune system, a disease state (e.g., cancer), or combinations or portions thereof. As one non-limiting example, multiple cells or tissues of the female reproductive tract can be cultured in the tissue culture platforms 10 described in the present disclosure using the culture systems described in U.S. Pat. No. 9,695,399, which is incorporated by reference in its entirety.

In some example configurations, the tissue culture platforms 10 described in the present disclosure can include on-board data acquisition components or systems. For instance, a tissue culture platform 10 can include components or systems that provide real-time monitoring of cell growth or culture conditions in one or more of the culture subsystems 38. The on-board data acquisition components or systems may include fiber optics, lenses, cameras, and so on (e.g., for optical monitoring within the tissue culture platform 10); probes, microparticles, antibodies, and so on (e.g., to detect the presence/absence/level of one or more factors in one or more of the culture subsystems 38); thermometers, pH monitors, and so on (e.g., to monitor media conditions); and other suitable data acquisition components or systems.

Additionally or alternatively, the tissue culture platforms 10 can be configured to include on-board heating elements, cooling elements, or both, that allow for controlling the temperatures in culture subsystems 38 in order to provide optimal temperatures for culture. In these instances, the tissue culture platforms 10 can also include on-board thermometers, thermostats, or both. In some embodiments, temperature regulation elements are linked to on-board controllers, processors, and so on, and desired temperatures may be changed in real-time (e.g., to reflect changes in biological conditions). As one example, the entire tissue culture platform 10 can be maintained at a single temperature. As another example, the temperature of each well chamber 16 or culture subsystem 38 can be separately regulated. In other instances, the temperature of the tissue culture platform 10 can be externally regulated.

In some embodiments, the tissue culture platforms 10 described in the present disclosure can include on-board components for maintaining, regulating, facilitating, or monitoring, the flow, culture conditions, and so on, of the various culture subsystems 38. Additionally or alternatively, one or more off-board components or systems can be used for maintaining, regulating, facilitating, or monitoring, the flow, culture conditions, and so on, of the various subsystems. Components and/or functions that may be housed off-board include, for example, temperature control elements, optics (e.g., cameras, microscope, fluorimeter) for monitoring conditions in chambers (e.g., through the transparent lid 26), batteries, user interface and/or controller(s) (e.g., connected wirelessly and/or by a physical connection to on-board electronic components, battery or other power source, media reservoir(s)).

The tissue culture platforms 10 and components thereof described in the present disclosure can be composed of suitable materials selected on the basis of porosity, permeability, weight, cost, sterilizability, 3D printability, reactivity, thermal transfer, transparency/opacity, and so on. Suitable materials include plastics, resins, glass, metals, films, membranes, and so on. In some embodiments, components of the tissue culture platforms 10 can be composed of one or more plastics including but not limited to phenol formaldehyde resin (e.g., Bakelite), neoprene, nylon, PVC, polystyrene, polyurethane, polyacrylonitrile, PVB, silicone, rubber, polyamide, synthetic rubber, vulcanized rubber, acrylic, polyethylene or high-density polyethylene ("HDPE"), polypropylene, polysulfone, polyethylene terephthalate, polytetrafluoroethylene ("PTFE"), polyether ether keytone ("PEEK"), polyether block amide (e.g., PEBAX), polycarbonate, and so on; non-plastic components, such as glass; metals, including but not limited to aluminum, antimony, boron, cadmium, cesium, chromium, cobalt, copper, gold, iron, lead, lithium, manganese, mercury, molybdenum, nickel, platinum, palladium, rhodium, silver, tin, titanium, tungsten, vanadium, zinc, and alloys thereof; or other suitable materials.

For example, in some implementations components of the tissue culture platforms 10 can be composed of polystyrene or other hydrophobic materials. In some other implementations, components of the tissue culture platforms 10 can be composed of hydrophobic materials that are treated to reduce their hydrophobicity. For instance, as one non-limiting example, hydrophobic materials can be treated using plasma treating to reduce their hydrophobicity in order to reduce the loss of hydrophobic compounds, such as hydrophobic hormones. Plasma treating may include plasma activation, plasma cleaning, plasma coating, plasma etching, or other suitable plasma treatment processes. In still other implementations, components of the tissue culture platforms 10 can be composed of hydrophilic materials, such as hydrophilic acrylic. In some implementations, a hydrophilic material may also be treated, such as plasma treated, to modify its hydrophilicity or hydrophobicity.

Advantageously, the tissue culture platforms 10 can be manufactured to allow for the use of media, such as hormones, without those media being absorbed and/or adsorbed into the components of the tissue culture platform 10. This enables to study of hormone transfer between well chambers 16 that would otherwise be compromised by using hydrophilic materials used in other conventional cell and tissue culturing devices. Likewise, using materials such as these prevents leeching of compounds from the tissue culture platform 10 into the media contained in the well chambers 16.

In some implementations, the tissue culture platforms 10 may also be adapted for use in non-tissue-culturing applications or other non-biological applications. For instance, the tissue culture platforms 10 may be adapted for use in ecological studies (e.g., of algal blooms in controlled microenvironments), or for studying organic, inorganic, or other chemical applications where precisely controlling the flow of chemical compounds between controlled microenvironments is desirable. In these instances, the materials from which the tissue culture platform 10 components are composed may be more relaxed than in the tissue and cell culturing applications. For instance, the metal and metal alloy materials described above could be used.

One or more surfaces of a component of the tissue culture platforms 10 described in the present disclosure can be coated to impart one or more desired characteristics, functionalities, or both. For example, a hydrophobic coating may be used on one or more surfaces of a component. Suitable hydrophobic coatings include paralyene, polytetrafluoroethylene, and so on. Similarly, the surfaces of the well chambers 16, channels 18, and so on, may be formed from non-adherent materials or may be coated with non-adherent materials to form a non-adherent surface. Examples of non-adherent materials include perfluorinated polymers, olefins, or like polymers or mixtures thereof. Other examples include agarose, non-ionic hydrogels such as polyacrylamides, polyethers such as polyethylene oxide, and polyols such as polyvinyl alcohol, or like materials or mixtures thereof.

As described above, one or more components of the tissue culture platforms 10 described in the present disclosure can also be plasma treated to modify the hydrophobicity or hydrophilicity of the components. For instance, the components could be treated using plasma activation, plasma cleaning, plasma coating, plasma etching, or any other suitable plasma treatment process.

The components of the tissue culture platforms 10 described in the present disclosure can be produced by known fabrication techniques, such as laser machining, injection molding, 3D-printing, hot embossing, additive manufacturing, lithography, milling, and so on.

The tissue culture platforms described in the present disclosure can find use in standard cell culture applications, standard tissue culture applications, drug toxicity studies, environmental toxicology studies, drug screening applications, disease modeling applications, tissue engineering applications, regenerative medicine applications, and so on.

As noted, the tissue culture platforms described in the present disclosure enable tissue or cell culture under customizable, dynamic flow conditions as opposed to static conditions of standard laboratory automation compatible plates. The tissue culture platforms described in the present disclosure also enable interaction of multiple tissue types, cell types, or both, as opposed to singular tissue/cell types of standard plates with capacity of up to 10 different connected cultures. The base station of the tissue culture platforms described in the present disclosure contains pump motor and electronics, and can easily be installed into standard and automated cell culture incubators.

Figure 10:
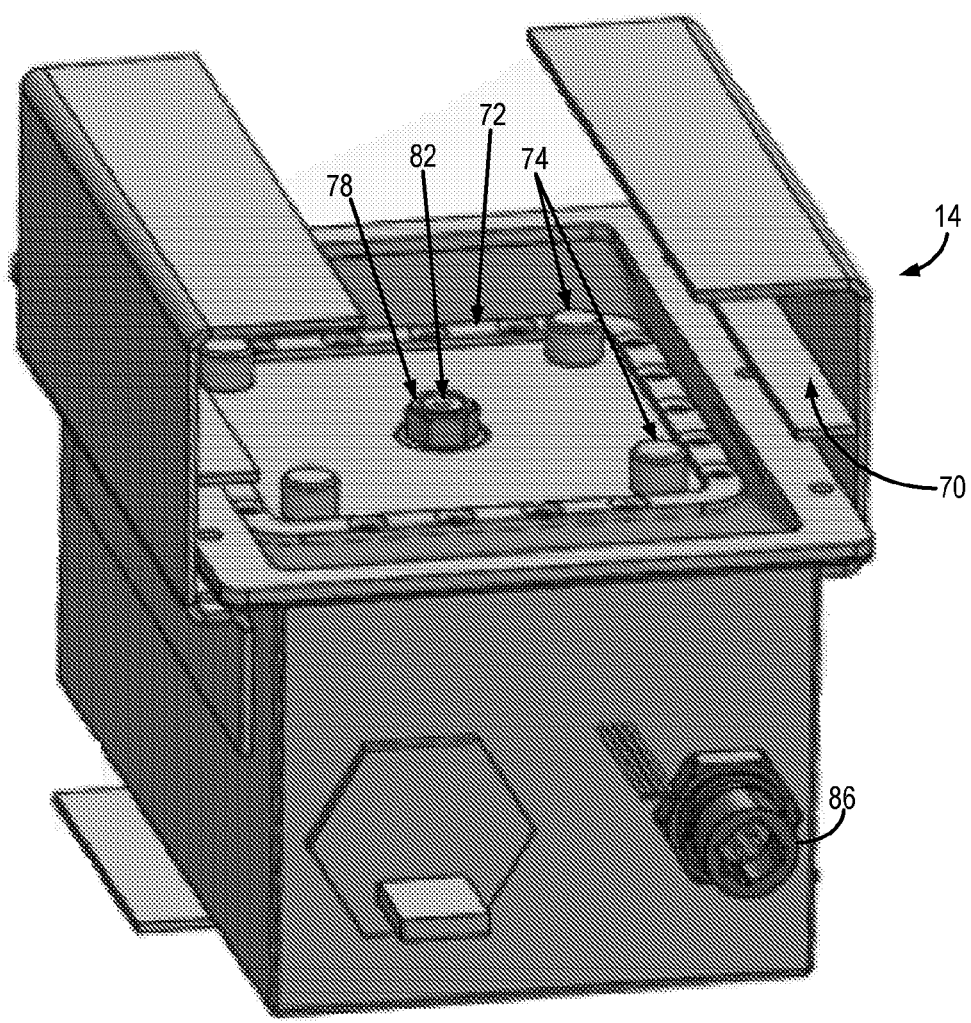
FIG. 10 shows an example of a base station having a stage that can be raised and lowered to engage and disengage, respectively, a base plate positioned in the base station.

An alternative configuration of a base station 14 for use with the tissue culture platforms 10 described in the present disclosure is shown in FIGS. 10-13. As shown in FIG. 10, the base station 14 can include a tray 70 that is sized to receive a base plate 12, such as by sliding the base plate 12 into the tray 70. A moveable stage 72 in the base station 14 can be raised (and lowered) to engage (or disengage) a base plate 12 that is positioned in the tray 70. For instance, a base plate 12 can be arranged in the tray 70 while the stage 72 is in a lowered position. The stage 72 is then raised to engage the base plate 12.

Figure 11:
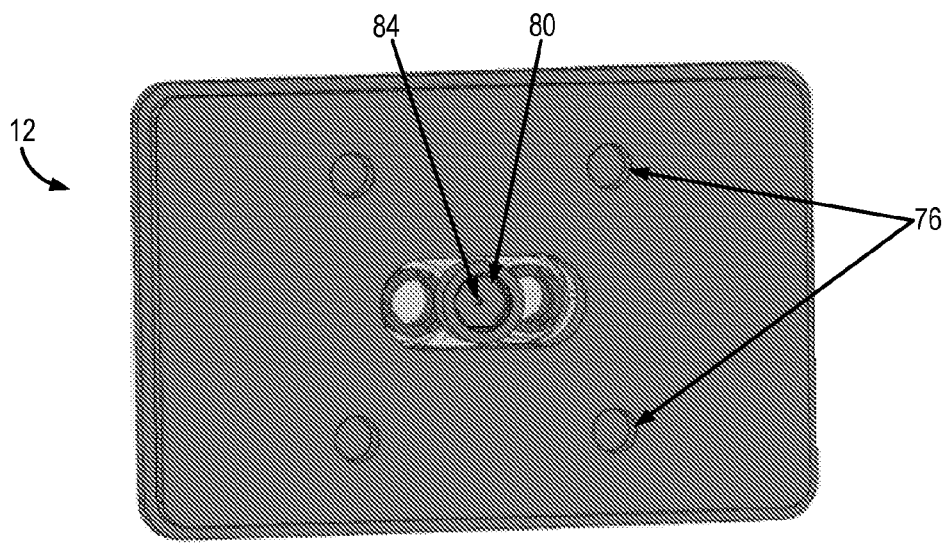
FIG. 11 shows an example of the bottom surface of a base plate that is configured to engage the moveable stage of the base station shown in FIG. 10.

The stage 72 can include one or more pins 74, which may also be tabs, posts, or other such structures, that engage similarly sized and shaped recesses 76 on the bottom surface of the base plate 12 (as shown in FIG. 11). The interfacing of the pins 74 and recesses 76 helps stabilize and reduce movement of the base plate 12.

The stage 72 also includes an interface 78 that couples the base plate 12 with the one or more motors 22 in the base station 14. For instance, the interface 78 can include a hexagonal or otherwise shaped pin, tab, post, or structure that engages a similarly sized and shaped recess 80 in the bottom surface of the base plate 12. The interface 78 can be rotated by operation of the one or more motors 22, such that rotation of the interface 78 when engaged with the base plate 12 causes the one or more selector valves 20 to be similarly rotated, thereby allowing for independent control of the fluid path between well chambers 16 in the base plate 12. The interface 78 can also include an aperture 82 that enables coupling of the pump source 28 to the selector valve 20 associated with the interface 78. Likewise, the recess 80 in the base plate 12 can include an aperture 84 that enables coupling of the pump source 28 to the selector valve 20 associated with the interface 78.

Figure 12:
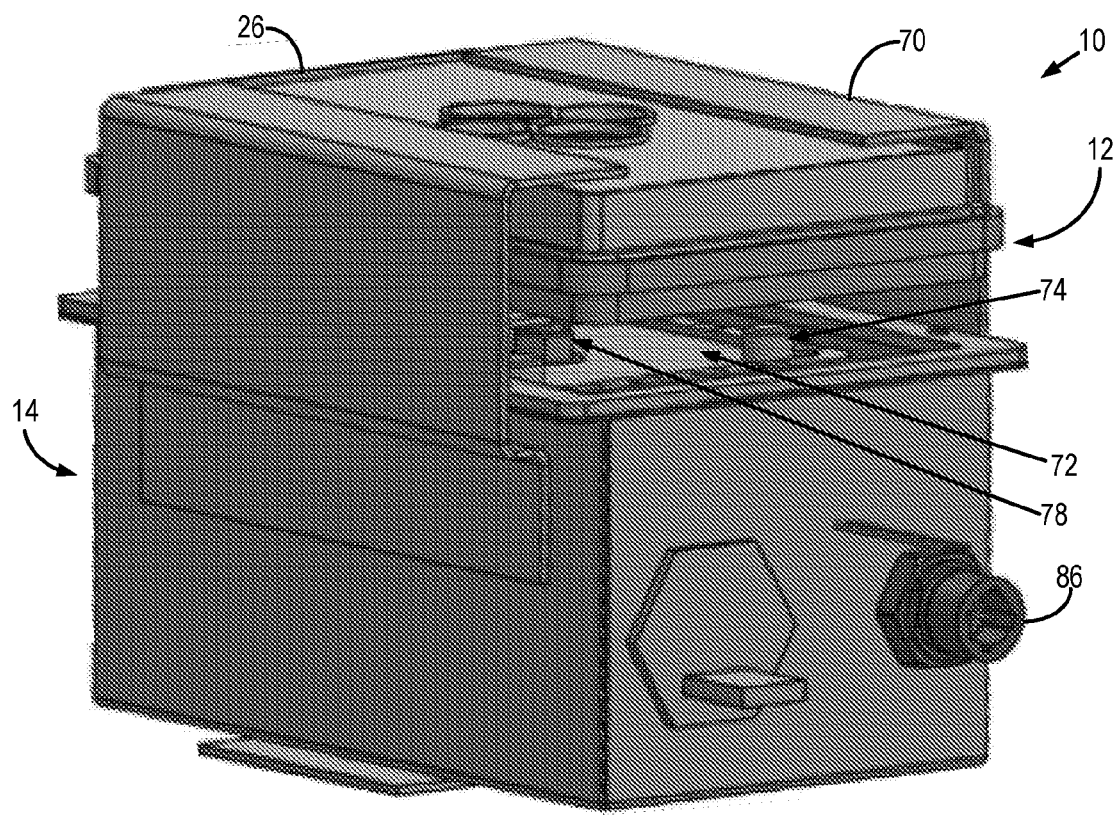
FIG. 12 shows an example of a base plate arranged within the base station of FIG. 10, in which the stage is in the lower position.
Figure 13:
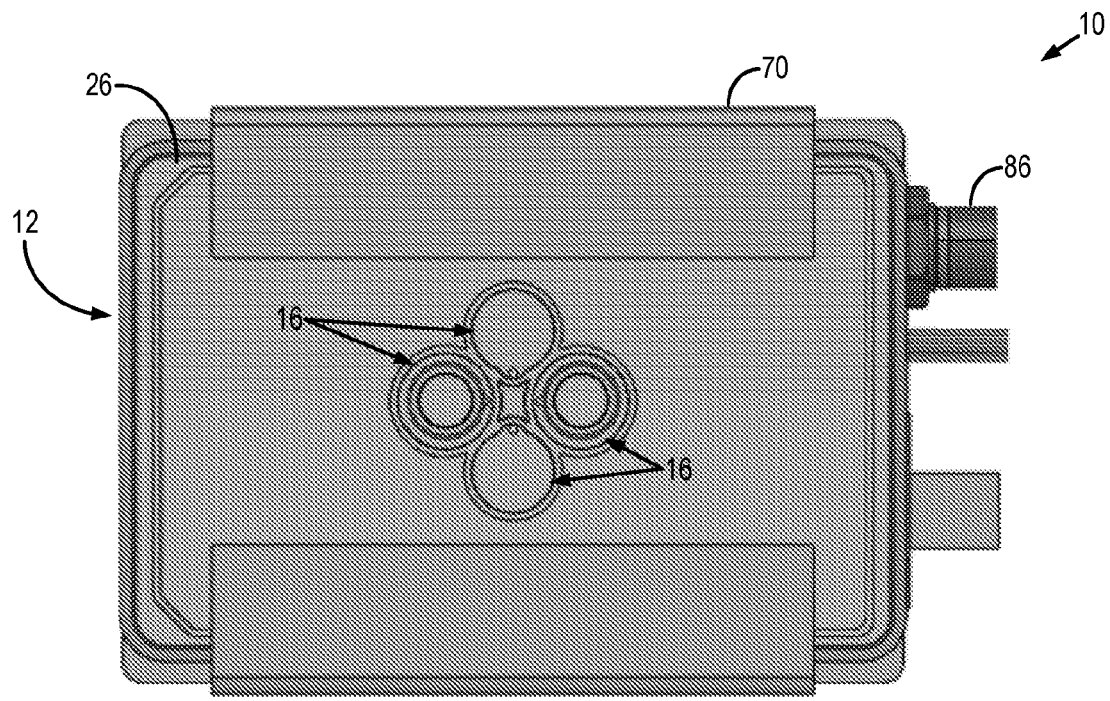
FIG. 13 shows another example of a base plate arranged within the base station of FIG. 10.

The base plate 12 shown in FIGS. 12 and 13 includes only a single culture subsystem 38; however, in configurations where the base plate 12 includes more than one culture subsystem 38 it will be appreciated that the base station 14 will include a similar number of interfaces 78 for engaging the base plate 12 to enable independent control the selector valves 20 associated with each culture subsystem 38.

An electrical connector 86 is provided in the base station 14 for connecting the internal components (e.g., motors 22, pump source 28,) of the base station 14 to a power source, external computer system or controller, or so on. In this way, the tissue culture platform 10 can make use of a simplified electrical connection that allows for multiple tissue culture platforms 10 to be used in a small space (e.g., an incubator).

Figure 14A:
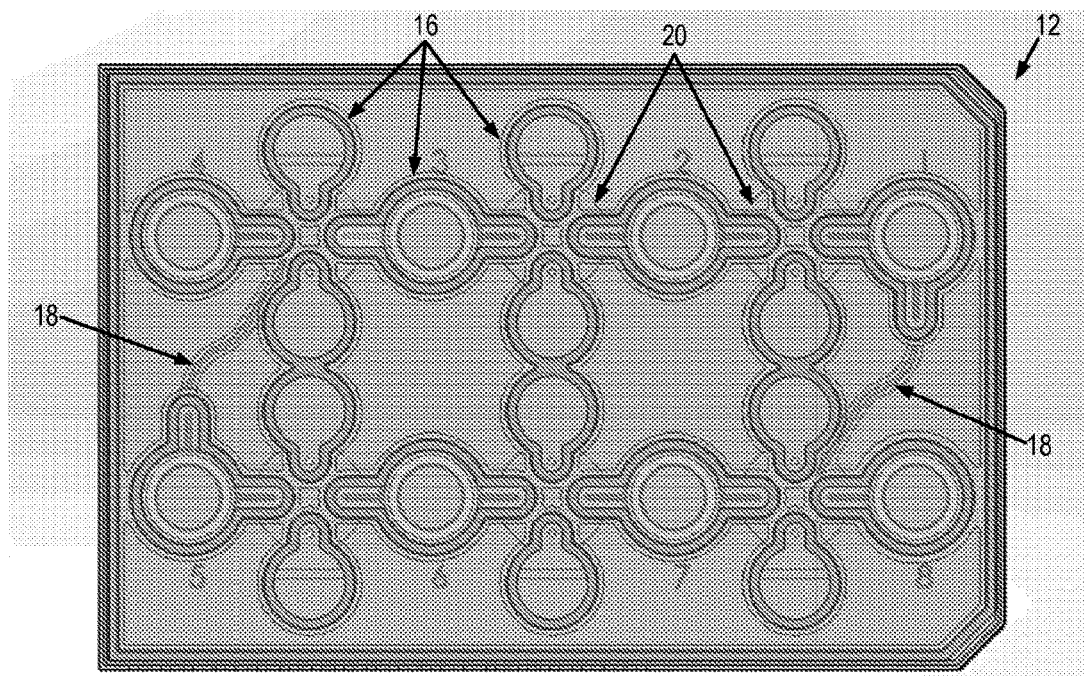
FIGS. 14A-14C show various views of another example of a base plate that can be used in the tissue culture assemblies described in the present disclosure.
Figure 14B:
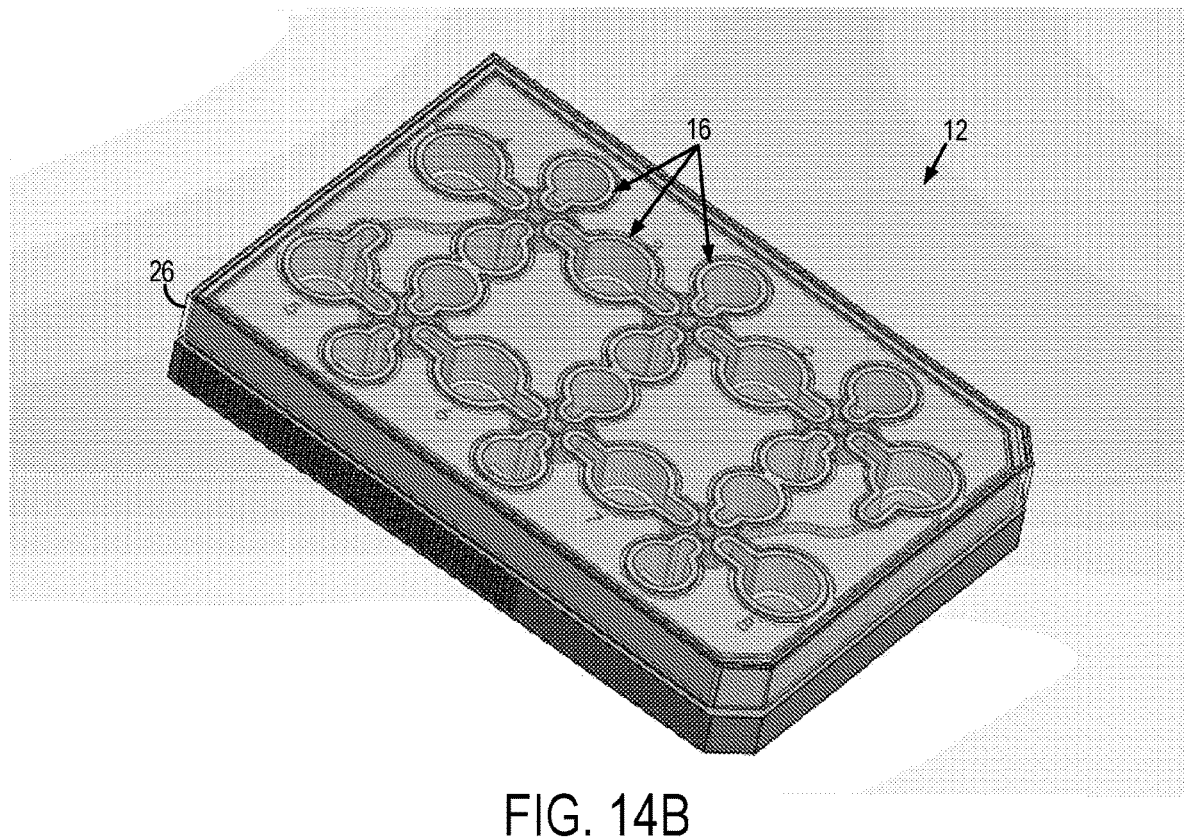
Figure 14C:
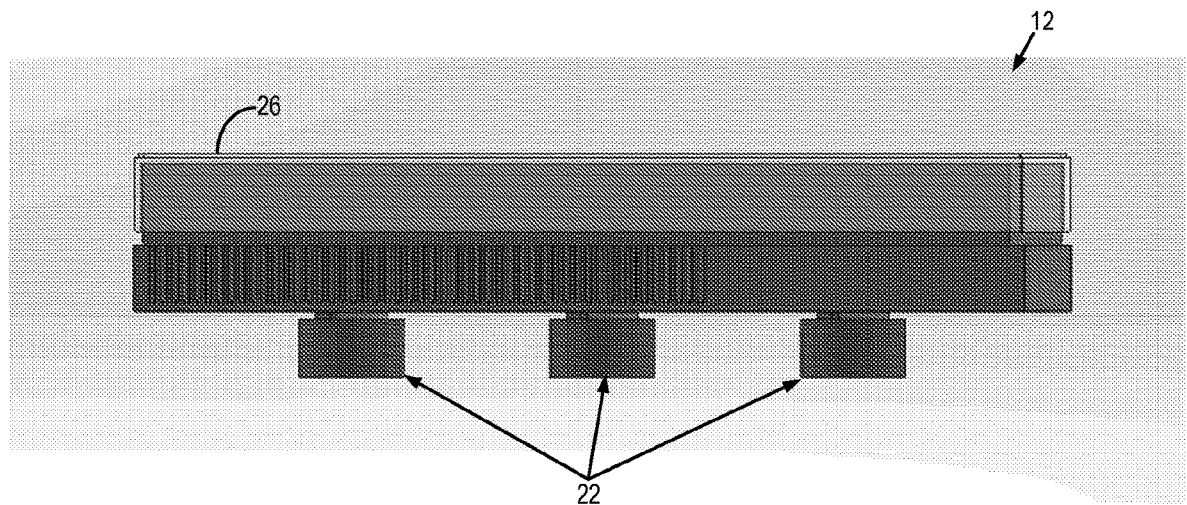

FIGS. 14A-14C show examples of alternative configurations of a base plate 12. In these examples, the base plate 12 includes eight different subculture systems 38. FIG. 14C shows motors 22 that are engaged with the base plate 12, such as described above, to enable operation of the associated selector valves 20 in order to independently control the fluid paths between well chambers in the base plate 12.

Figure 15:
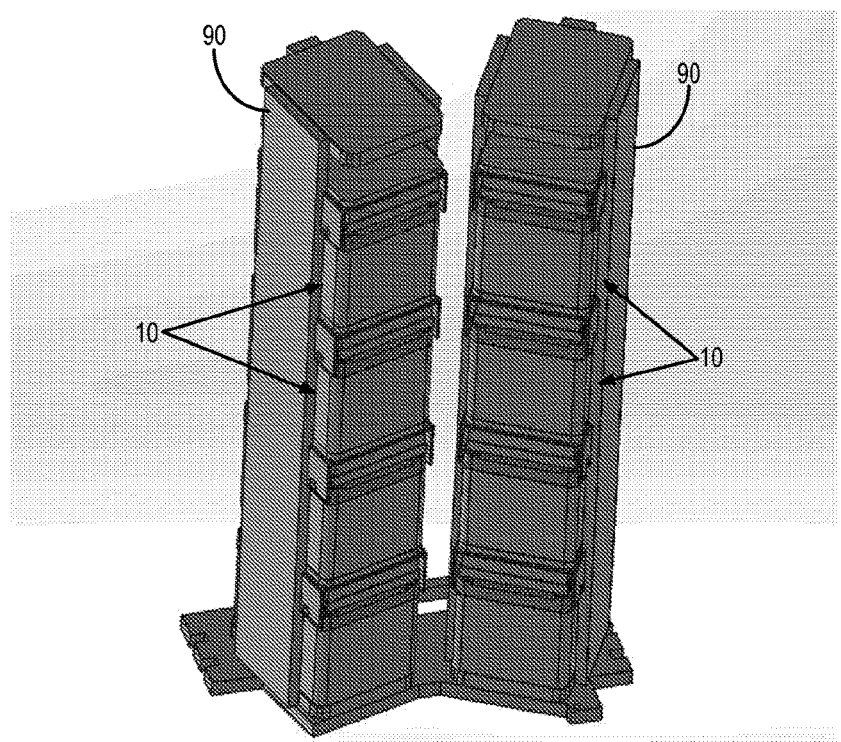
FIG. 15 shows an example of multiple tissue culture systems, or assemblies, arranged in a stacked arrangement in racks.

FIG. 15 shows an example of multiple tissue culture systems 10 arranged in a rack 90, which can enable multiple different culture experiments to be run in parallel. As described above, the tissue culture systems 10 can include a single, simple electrical connection that facilitates their use in such stacked arrangements. Tissue culture systems 10 can be added to and removed from the rack 90 using robotic handling, such as using standard or customized robotic handling equipment and systems.

Figure 16:
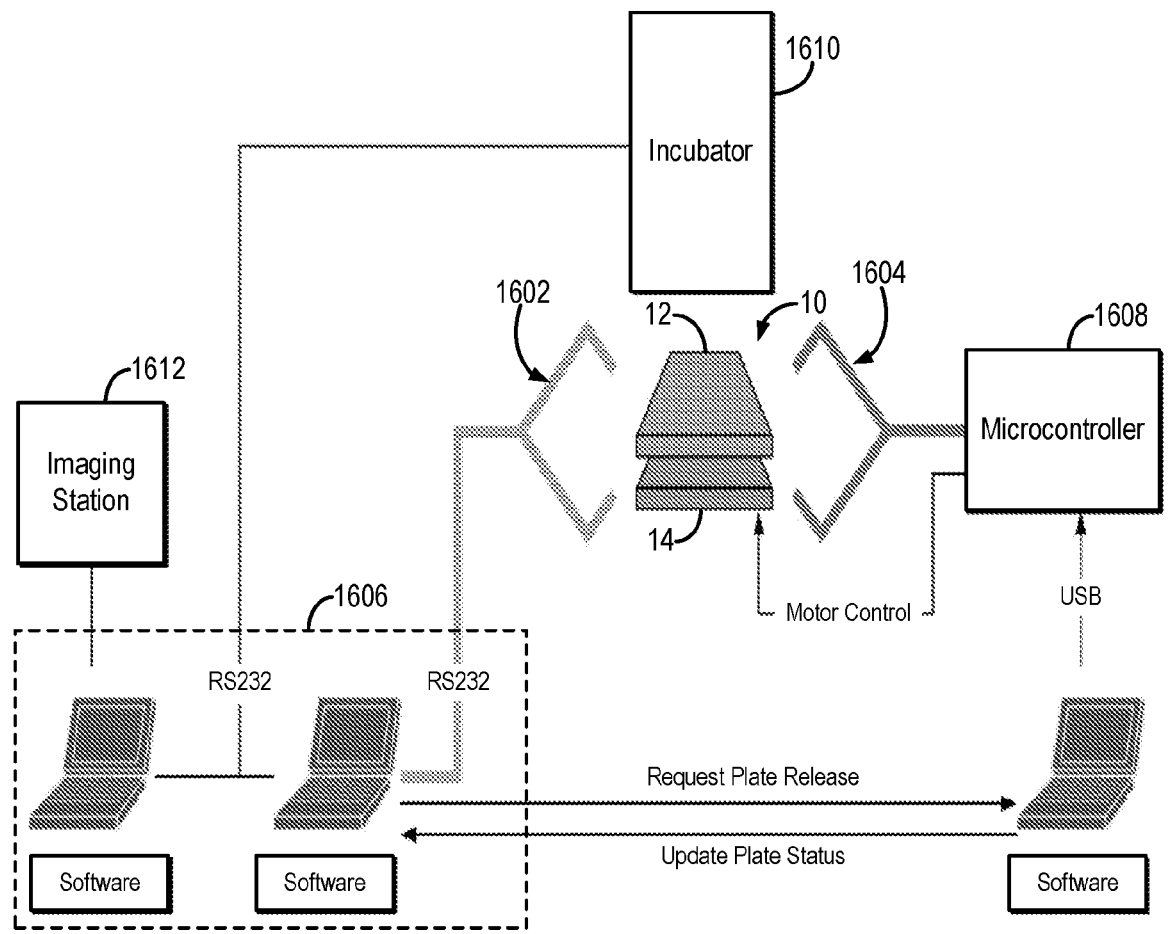
FIG. 16 shows a block diagram of an example system for robotic handling of one or more tissue culture platforms in accordance with some embodiments described in the present disclosure.

In some implementations, the tissue culture platforms 10 can be adapted for use with standard or customized robotic handling equipment and systems. In such instances, the tissue culture platforms 10 can be used to provide high-throughput analysis using integrated and simplified electronics. An example of such a system is illustrated in FIG. 16. A tissue culture platform 10 can be robotically handled via a robotic arm 1602 and a clamp 1604. The robotic arm 1602 can be controlled by a controller 1606, which may include one or more processors, a computer system, one or more application specific integrated circuits ("ASICs") or the like. The controller 1606 can also control the operation of an incubator 1610 and an imaging station 1612. In some instances, the controller 1606 can include more than one controller, such that a separate controller is used to operate each of the robotic arm 1602, the incubator 1610, and the imaging station 1612. In these instances, the multiple controllers can be in communication with each other. The clamp 1604 can be controlled by a microcontroller 1608, which may in some instances be the controller 24 described above for controlling the operation of the tissue culture platform 10. In this way, the microcontroller 1608 may also provide motor control and pump control for the tissue culture platform 10.

The robotic arm 1602 is operable under control of the robotic arm controller 1606 to transfer the tissue culture platform 10 between different locations, such as from an incubator 1610 to an imaging station 1612 or other suitable location. The clamp 1604 may be operable to secure the base plate 12 and base station 14 together for safe handling and transfer of the tissue culture platform 10. For instance, clamping the base plate 12 and the base station 14 together may include raising the stage 72 of a base station 14 to engage a base plate 12 that is positioned in a tray 70 of the base station. In this way, raising the stage 72 of the base station 14 to hold the base plate 12 against an upper surface of the tray 70 acts as the clamp 1604.

In some implementations, multiple tissue culture platforms 10 can be arranged in a tray, rack, or other suitable arrayed holder, such that multiple tissue culture platforms 10 can be transferred from an incubator 1610 to other location, such as imaging station 1612. This configuration further assists with providing a high throughput system. In these and other implementations, the base station 14 for the tissue culture platform 10 may reside in the incubator 1610 such that only the base plate 12 is transferred between the incubator 1610 and other location, such as the imaging station 1612.

Figure 17:
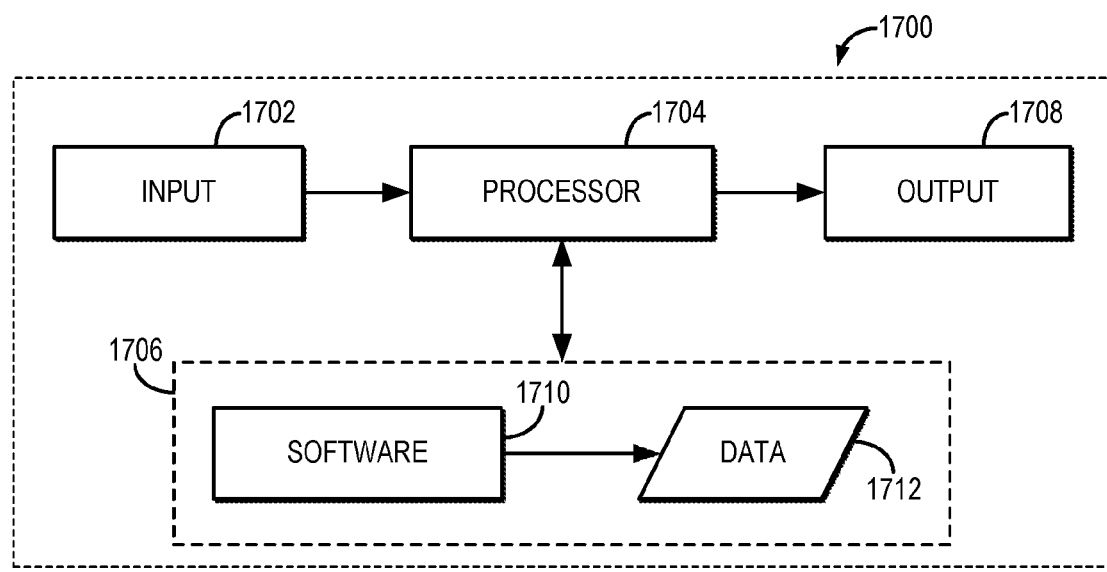
FIG. 17 shows a block diagram of an example computer system, which may be used to control operation of one or more selector valves in a tissue culture platform in order to control system flow therethrough.

Referring now to FIG. 17, a block diagram of an example of a computer system 1700 that can be implemented as the controller 24 of the tissue culture platforms 10 described in the present disclosure is shown. The computer system 1700 generally includes an input 1702, at least one hardware processor 1704, a memory 1706, and an output 1708. Thus, the computer system 1700 is generally implemented with one or more hardware processors 1704 and a memory 1706.

In some embodiments, the computer system 1700 can be an on-board circuit board housed within the base station 14 of the tissue culture platform 10. The computer system 1700 may also be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 1700 may operate autonomously or semi-autonomously, or may read executable software instructions from the memory 1706 or a computer-readable medium (e.g., a hard drive, a CD-ROM, flash memory), or may receive instructions via the input 1702 from a user, or any another source logically connected to a computer or device, such as another networked computer or server. Thus, in some embodiments, the computer system 1700 can also include any suitable device for reading computer-readable storage media.

In general, the computer system 1700 is programmed or otherwise configured to control the system flow in the tissue culture platform 10. For instance, the computer system 1700 can be programmed to control the operation of selector valves 20 in order to modify the fluid paths between well chambers 16, and to control the rate of flow in those fluid paths.

The input 1702 may take any suitable shape or form, as desired, for operation of the computer system 1700, including the ability for selecting, entering, or otherwise specifying parameters consistent with performing tasks, processing data, or operating the computer system 1700. In some aspects, the input 1702 may be configured to receive data or programming instructions, such as instructions defining the system flow parameters for one or more tissue culture or cell culture experiments. In addition, the input 1702 may also be configured to receive any other data or information considered useful for controlling the system flow or other operation of the tissue culture platform 10. The input 1702 may include, for instance, a wired or wireless connection.

The memory 1706 may contain software 1710 and data 1712, such as data acquired with on-board sensors associated with the tissue culture platform 10, and may be configured for storage and retrieval of processed information, instructions, and data to be processed by the one or more hardware processors 1704. In some aspects, the software 1710 may contain instructions directed to controlling the system flow or other operation of the tissue culture platform 10.

In addition, the output 1708 may take any shape or form, as desired. The output 1708 may include, for instance, a wired or wireless connection for communicating data 1712 stored on the memory 1706.

The software 1710 may include custom control software for controlling the operation of the tissue culture platform 10. For instance, the software 1710 may provide motor control, pump control, or both, such that the flow rate, volume transfer, and other parameters and properties of the tissue culture platform 10 can be individually controlled for one or more well chambers 16. The software 1710 may in some instances provide a graphical user interface ("GUI") that enables user interaction and input for controlling the operation of the tissue culture platform 10. The GUI may also output data and other information about the status of the tissue culture platform 10, including run time, temperature, volume transfer data, flow rate data, media content in various well chambers, and so on. The software 1710 can provide control on one tissue culture platform 10 or multiple different tissue culture platforms 10. The software 1710 can also provide independent control of one or more culture subsystems 38 within a given tissue culture platform.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A tissue culture assembly, comprising:
a base plate;
a plurality of culture subsystems coupled to the base plate, each culture subsystem comprising:
a plurality of well chambers;
a plurality of channels;
a selector valve fluidically coupling the plurality of well chambers via the plurality of channels;
wherein the selector valve is operable to modify a fluid path to facilitate exchange of media within a given culture subsystem or between culture subsystems of the plurality of culture subsystems;
a base station comprising:
an enclosure;
a plurality of motors housed in the enclosure; and
wherein, the base plate is removably coupled to the base station;
wherein each selector valve is a pneumatically actuated selector valve, and further comprising a pump source housed in the enclosure of the base station, the pump source being operable to pneumatically actuate each selector valve.

2. The tissue culture assembly of claim 1, wherein the plurality of well chambers comprises at least one culture well, at least one donor well, and at least one acceptor well.

3. The tissue culture assembly of claim 1, wherein the selector valve is a pneumatically actuated selector valve comprising a reservoir and a flexible membrane, wherein the selector valve is operable to modify the fluid path by modifying a pressure in the reservoir to deflect the flexible membrane.

4. The tissue culture assembly of claim 1, wherein the first well chamber is in a first culture subsystem and the second well chamber is in a second culture subsystem.

5. The tissue culture assembly of claim 1, wherein the first well chamber and the second well chamber are in a single culture subsystem.

6. The tissue culture assembly of claim 1, wherein the selector valve is operable to modify the fluid path to recirculate within a selected well chamber.

7. The tissue culture assembly of claim 1, wherein the selector valve in each of the plurality of culture subsystems is operable to facilitate exchange of media between the culture subsystems to define a plurality of integrated culture subsystems.

8. The tissue culture assembly of claim 1, wherein the selector valve in each of the plurality of culture subsystems is operable to facilitate exchange of media within each culture subsystem while preventing exchange of media between the culture subsystems in order to define a plurality of non-interacting culture subsystems.

9. The tissue culture assembly of claim 1, wherein the selector valve in each of the plurality of culture subsystems is operable to facilitate exchange of media between the culture subsystems to define a plurality of integrated culture subsystems.

10. The tissue culture assembly of claim 1, wherein the selector valve is a rotary valve that is operable to change the fluid path between well chambers by rotating the rotary valve.

11. The tissue culture assembly of claim 1, further comprising a base station comprising:
an enclosure;
a plurality of motors housed in the enclosure; and
wherein, the base plate is removably coupled to the base station.

12. The tissue culture assembly of claim 11, wherein each of the plurality of motors operatively engages one of the selector valves when the base plate is removably coupled to the base station.

13. The tissue culture assembly of claim 12, further comprising a controller that controls an operation of the plurality of motors to adjust the fluid path defined by each selector valve.

14. The tissue culture assembly of claim 13, wherein each selector valve is a rotary valve that is operable to change the fluid path between well chambers by rotating the rotary valve through operation of each respective one of the plurality of motors.

15. The tissue culture assembly of claim 11, wherein each selector valve is a pneumatically actuated selector valve, and further comprising a pump source housed in the enclosure of the base station, the pump source being operable to pneumatically actuate each selector valve.

16. The tissue culture assembly of claim 11, wherein the base station further comprises a slot that receives the base plate.

17. The tissue culture assembly of claim 16, wherein the slot comprises a tray.

18. The tissue culture assembly of claim 16, wherein the base station further comprises a stage that is moveable between a lowered position and a raised position, such that when in the raised position the stage engages the base plate when the base plate is positioned in the slot.

19. The tissue culture assembly of claim 18, wherein the stage includes an interface that extends from an upper surface of the stage to engage a recess formed in a lower surface of the base plate.

20. The tissue culture assembly of claim 19, wherein the interface is a actuatable interface such that actuation of the interface when the stage is engaged with the base plate causes the selector valve to modify the fluid path to facilitate exchange of media within the given culture subsystem or between culture subsystems.

21. The tissue culture assembly of claim 20, wherein the actuatable interface is a rotatable interface and actuation of the interface comprises rotation of the interface.

22. The tissue culture assembly of claim 19, wherein the interface includes a first aperture coupled to a pump source, and the recess includes a second aperture coupled to the selector valve, such that when the stage is engaged with the base plate that first aperture and the second aperture are coupled such that operation of the pump source causes the selector value to open and close the fluid path.

23. The tissue culture assembly of claim 1, wherein the plurality of channels comprises a plurality of microfluidic channels.

24. The tissue culture assembly of claim 23, wherein the plurality of microfluidic channels are formed in the base plate.

25. The tissue culture assembly of claim 1, wherein at least the plurality of well chambers and the plurality of channels are composed of a hydrophobic material.

26. The tissue culture assembly of claim 25, wherein the hydrophobic material is polystyrene.

27. The tissue culture assembly of claim 25, wherein the hydrophobic material is treated to reduce its hydrophobicity.

28. The tissue culture assembly of claim 27, wherein the hydrophobic material is treated using a plasma treating to reduce its hydrophobicity.

29. The tissue culture assembly of claim 1, wherein at least the plurality of well chambers and the plurality of channels are composed of hydrophilic acrylic.

30. A tissue culture assembly, comprising:
a base plate;
a plurality of culture subsystems coupled to the base plate, each culture subsystem comprising:
   a plurality of well chambers;
   a plurality of channels;
   a selector valve fluidically coupling the plurality of well chambers via the plurality of channels;
a base station comprising:
   an enclosure;
   a plurality of motors housed in the enclosure;
   wherein, the base plate is removably coupled to the base station;
   wherein the selector valve is operable to modify a fluid path to facilitate exchange of media within a given culture subsystem or between culture subsystems of the plurality of culture subsystems;
   wherein the base station further comprises a slot that receives the base plate;
   wherein the base station further comprises a stage that is moveable between a lowered position and a raised position, such that when in the raised position the stage engages the base plate when the base plate is positioned in the slot;
   wherein the stage includes an interface that extends from an upper surface of the stage to engage a recess formed in a lower surface of the base plate; and
   wherein the interface includes a first aperture coupled to a pump source, and the recess includes a second aperture coupled to the selector valve, such that when the stage is engaged with the base plate that first aperture and the second aperture are coupled such that operation of the pump source causes the selector value to open and close the fluid path.

31. The tissue culture assembly of claim 1, wherein the selector valve is operable between an open state and a closed state, such that when in the open state the selector valve modifies the fluid path to fluidically couple a first well chamber to a second well chamber of the plurality of well chambers via ones of the plurality of channels in fluid communication with the selector valve, the first well chamber, and the second well chamber.

32. The tissue culture assembly of claim 31, wherein the selector valve is further operable to modify a flow rate through the fluid path when the selector valve is in the open state.

* * * * *